US010905712B2

(12) United States Patent
Stenzler et al.

(10) Patent No.: US 10,905,712 B2
(45) Date of Patent: *Feb. 2, 2021

(54) COMPOSITIONS AND METHODS FOR TREATING DISEASES OR DISORDERS USING EXTENDED RELEASE NITRIC OXIDE RELEASING SOLUTIONS

(71) Applicant: SaNOtize Research and Development Corp., Vancouver (CA)

(72) Inventors: Alex Stenzler, Long Beach, CA (US); Christopher C. Miller, North Vancouver (CA); Gilly Regev-Shoshani, Vancouver (CA)

(73) Assignee: SaNOtize Research and Development Corp., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/675,773

(22) Filed: Aug. 13, 2017

(65) Prior Publication Data

US 2018/0125882 A1 May 10, 2018

Related U.S. Application Data

(63) Continuation of application No. 14/643,305, filed on Mar. 10, 2015, now Pat. No. 9,730,956.

(60) Provisional application No. 61/953,053, filed on Mar. 14, 2014.

(51) Int. Cl.
| | | |
|---|---|---|
| A61K 33/00 | (2006.01) | |
| C01B 21/24 | (2006.01) | |
| A61K 9/00 | (2006.01) | |
| A61K 47/12 | (2006.01) | |
| A61K 9/08 | (2006.01) | |
| A61K 9/70 | (2006.01) | |

(52) U.S. Cl.
CPC .......... *A61K 33/00* (2013.01); *A61K 9/0043* (2013.01); *A61K 9/08* (2013.01); *A61K 9/7007* (2013.01); *A61K 47/12* (2013.01); *C01B 21/24* (2013.01)

(58) Field of Classification Search
None
See application file for complete search history.

(56) References Cited

U.S. PATENT DOCUMENTS

| | | |
|---|---|---|
| 6,709,681 B2 | 3/2004 | Benjamin et al. |
| 7,040,313 B2 | 5/2006 | Fine et al. |
| 2004/0161452 A1 | 8/2004 | Petit |
| 2005/0036949 A1 | 2/2005 | Tucker et al. |
| 2005/0037093 A1 | 2/2005 | Benjamin |
| 2005/0089554 A1 | 4/2005 | Cormier et al. |
| 2006/0105028 A1 | 5/2006 | Zhang et al. |
| 2007/0116785 A1 | 5/2007 | Miller |
| 2009/0196930 A1 | 8/2009 | Surber et al. |
| 2010/0040703 A1 | 2/2010 | Miller et al. |
| 2010/0262095 A1 | 10/2010 | Hall |
| 2012/0003293 A1* | 1/2012 | Miller .................. A43B 1/0045 424/445 |
| 2013/0330244 A1 | 12/2013 | Balaban et al. |
| 2015/0157657 A1* | 6/2015 | Stenzler ................ A61M 35/00 128/200.22 |

FOREIGN PATENT DOCUMENTS

| | | |
|---|---|---|
| WO | WO 2003/013489 A1 | 2/2003 |
| WO | WO 2003/020211 A2 | 3/2003 |
| WO | WO 2008116497 A1 | 10/2008 |
| WO | WO 2009/086470 A2 | 7/2009 |
| WO | WO 2011/085484 A1 | 7/2011 |
| WO | WO 2012052561 A2 | 4/2012 |

(Continued)

OTHER PUBLICATIONS

Adam et al.; "A Clinical Trial of Hypertonic Saline Nasal Spray in Subjects With the Common Cold or Rhinosinusitis"; Archives of Family Medicine; (Jan.-Feb. 1998); pp. 39-43; vol. 7, No. 1.

Regev-Shoshani et al.; "Safety, bioavailability and mechanism of action of nitric oxide to control Bovine Respiratory Disease Complex in calves entering a feedlot"; Research in Veterinary Science; (Apr. 2014); pp. 328-337; vol. 96, No. 2.

Regev-Shoshani et al.; "Prophylactic nitric oxide treatment reduces incidence of bovine respiratory disease complex in beef cattle arriving at a feedlot"; Research in Veterinary Science; (Oct. 2014); pp. 606-611; vol. 95, No. 2.

(Continued)

*Primary Examiner* — Susan T Tran
(74) *Attorney, Agent, or Firm* — Thorpe North & Western, LLP; David W. Osborne

(57) ABSTRACT

The present invention relates to a liquid nitric oxide releasing solution (NORS) comprised of at least one nitric oxide releasing compound and at least one acidifying agent, wherein the NORS provides an extended release of a therapeutically effective amount of nitric oxide gas (gNO). The present invention also relates to a liquid NORS comprised of at least one nitrite compound having a concentration of no greater than about 0.5% w/v and at least one acidifying agent, wherein the NORS releases a therapeutically effective amount of gNO. The present invention also relates to a method for the treatment of a wound in a human, the method comprising administering to the human a liquid NORS comprised of at least one nitric oxide releasing compound and at least one acidifying agent, wherein the NORS provides an extended release of a therapeutically effective amount of gNO. The present invention also relates to a method for the treatment, prevention, or reduction of incidence of a disease or disorder in a human in need thereof, the method comprising administering to the human a liquid NORS comprised of at least one nitrite compound at a concentration of no greater than about 0.5% w/v and at least one acidifying agent, wherein the NORS releases a therapeutically effective amount of gNO.

13 Claims, 19 Drawing Sheets

(56) References Cited

FOREIGN PATENT DOCUMENTS

WO     WO 2015006528 A1     1/2015
WO     WO 2017037684 A1     3/2017

OTHER PUBLICATIONS

Regev-Shoshani et al.; "A nitric oxide-releasing solution as a potential treatment for fungi associated with tinea pedis"; Journal of Applied Microbiology; (Feb. 2013); pp. 536-544; vol. 114, No. 2.
Taylor et al.; "Early Results Using a Dynamic Method for Delayed Primary Closure of Fasciotomy Wounds"; Journal of American College of Surgeons; (Nov. 2003); pp. 872-878; vol. 197, No. 5.
Weller et al.; "The effects of topical treatment with acidified nitrite on would healing in normal and diabetic mice"; Nitric Oxide; (Apr. 27, 2006); pp. 395-399; vol. 15.

* cited by examiner

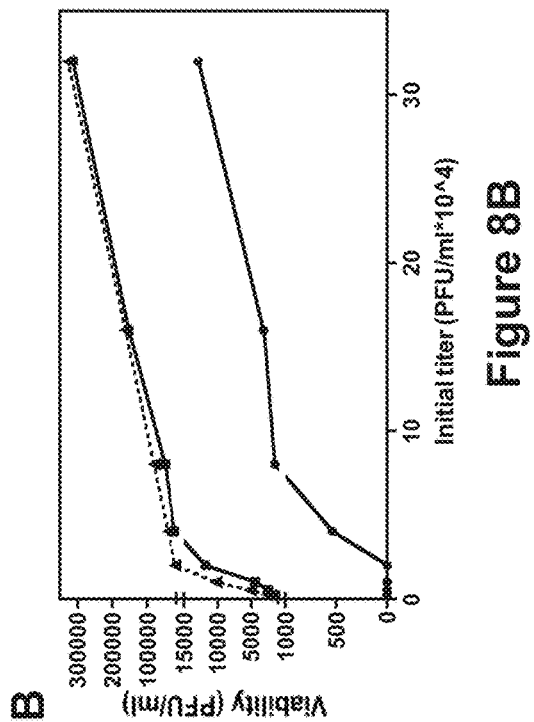
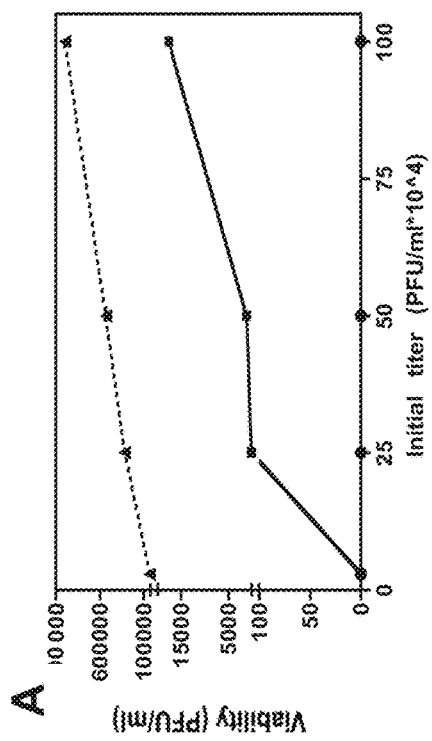
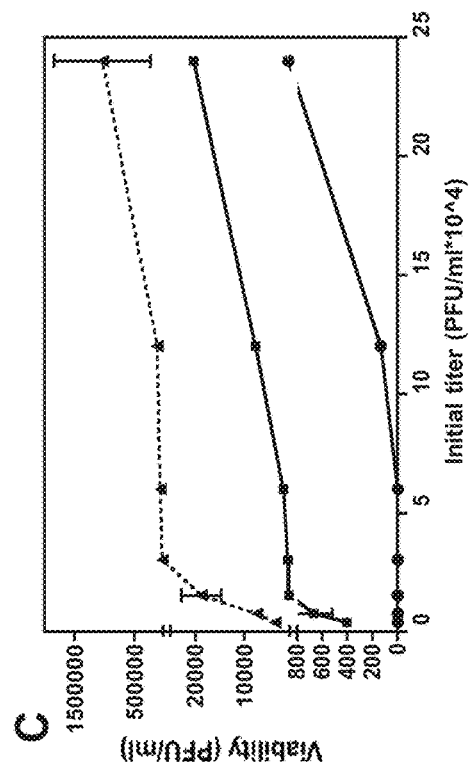
Figure 8A
Figure 8B
Figure 8C

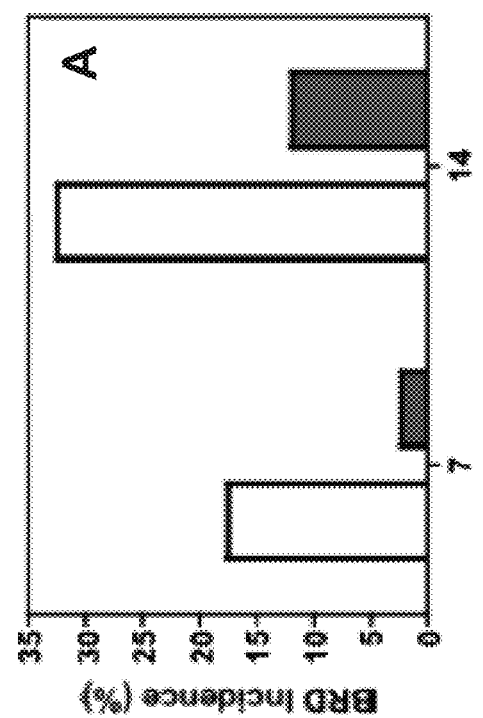
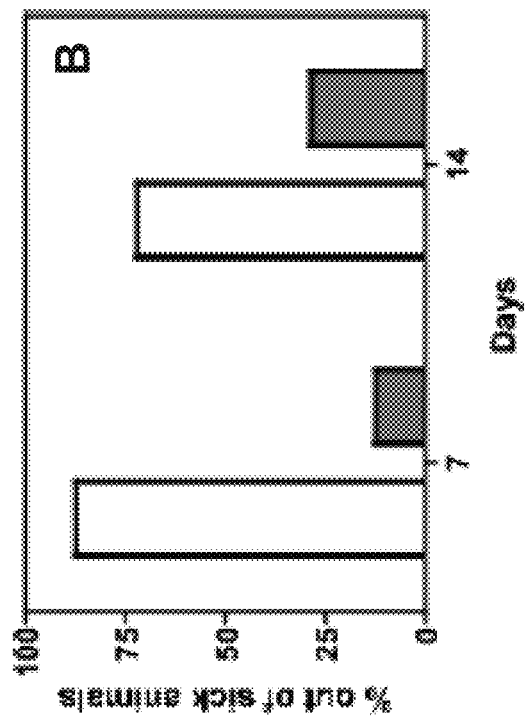
Figure 13A
Figure 13B

COMPOSITIONS AND METHODS FOR TREATING DISEASES OR DISORDERS USING EXTENDED RELEASE NITRIC OXIDE RELEASING SOLUTIONS

CROSS-REFERENCE TO RELATED APPLICATIONS

This application is a continuation of U.S. patent application Ser. No. 14/643,305, filed Mar. 10, 2015, now issued as U.S. Pat. No. 9,730,956, which claims priority to U.S. Provisional Patent Application No. 61/953,053, filed Mar. 14, 2014, each of which is incorporated herein by reference in their entirety.

BACKGROUND OF THE INVENTION

Endogenous NO has been shown to play a critical role in various bodily functions, including the vasodilatation of smooth muscle, neurotransmission, regulation of wound healing and immune responses to infection such as bactericidal action directed toward various organisms (Moncada et al., 1991, Pharmacol Rev, 43: 109-42; De Groote et al., 1995, Clin Infect Dis, 21(suppl 2): S162-164).

NO is a free-radical which is lipophilic with a small stokes radius making it an excellent signally molecule enabling it to readily cross the plasma membrane into the cytosol, and is therefore believed to be suitable for treatment of a variety of indications. For example, NO has been demonstrated to play an important role in wound healing through vasodilatation, angiogenesis, anti-inflammatory and antimicrobial action (Witte et al., 2002, Amer J of Surg, 183: 406-12). It is hypothesized that the antimicrobial and cellular messenger regulatory properties of this molecule, delivered in an exogenous gaseous form, might easily enter the wound milieu and be useful in optimizing the healing of chronic wounds with specific actions directed at reducing bacterial burden, reducing exudate and improving endogenous debridement.

Further, the therapeutic potential of NO donors for cutaneous lesions, as a broad-spectrum antimicrobial seems promising (Fang, 1997, Amer Soc Clin Invest, 33: 2818-25; Vazquez-Torres et al., 1999, Nitric Oxide and Infection, 475-88). However, to date, this approach has not been realized in clinical commercial applications. This may be due to the toxic side effects of the carrier compounds of solid, liquid, cream, or other non-gaseous NO donors and specifically, the acidic environment required for release of the NO molecule (Omerod et al., 1999, J Invest Dermatol, 113: 392-7; Bauer et al., 1998, Wound Repair Regen, 6: 569-77). Adequate efficacy also may not have been demonstrated due to binding of the nitric oxide with other compounds in the preparations. Endogenous approaches such as intracellular nitric oxide synthase (NOS) stimulation and exogenous wound dressings with either NO-donors or saturated NO-containing solutions have also failed to release consistent steady-state concentrations of NO (Shabini et al., 1996, Wound Repair Regen, 4: 353-63). Direct exposure to nitric oxide gas has been used (Stenzler, U.S. Pat. Nos. 6,643,2077, 7,892,198, 7,520,1866 and Miller, et al., 2004, J Cutaneous Med Surg 233-238) to treat wound infections, and while effective, requires that the patient be connected to a gas cylinder for 8 hours at a time for treatment. As such, these methods are not suitable or effective in situations when only a very short time is available for administration of the molecule.

Weller, and colleagues, describes a system using inorganic nitrite and an organic acid to produce NO on the skin surface (Weller et al., 1998, J Am Acad Dermatol, 38: 559-63). However, they describe the system as messy, impractical, causing pain in open wounds and possibly causing further damage to wounds. Hardwick, et al., refined the system using a selectively permeable membrane between the reactants and the wound. They reported that in an in vitro model it was effective at reducing microbial load (Hardwick et al., 2011, Clinical Sci, 100: 395-400). While this method for NO formation can be administered through topical application to a lesion or site of infection (Benjamin et al., U.S. Pat. No. 6,709,681), this treatment method is a short duration exposure, requiring multiple reapplications and is unlikely to treat lesions or infections that are not present at the specific site of application.

Thus, there is a need in the art for simple and effective non-antibiotic based treatments for humans, particularly in instances where the time or window available for administration is short, and where the targeted treatment site is different than the site of administration. The present invention addresses these unmet needs in the art.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 8A-8C are graphs depicting the viability of virus using NORS at 0.41% and different initial titers for control (triangle), 1 minute treatment (square) and 10 minutes treatment (circle). Saline was used as control. (A —IBR, B—BRSV, C—PI3).

FIGS. 13A-13B depicts the incidence of BRDc after 7 and 14 days post arrival to feedlot. FIG. 13A is a graph depicting the percentage of sick animals in each group. FIG. 13B is a graph depicting the percentage of sick animals in the treatment/control group out of total sick animals. White=control. Grey=NO treatment.

FIG. 14A is a graph depicting MetHb levels before, 5 minutes, and 30 minutes after treatment for the control animals. FIG. 14B is a graph depicting MetHb levels before, 5 minutes, and 30 minutes after treatment for the NO treated animals. FIG. 14C is a graph depicting the average difference in MetHb values 5 minutes and 30 minutes post treatment compared to the values measured before treatment. (grey=control, white=NO treatment) all animals tested in each group.

FIG. 15A is a spectrum depicting the exhaled NO of the control group. FIG. 15B is a spectrum depicting the exhaled NO of the treatment group.

DETAILED DESCRIPTION

Figure 1:
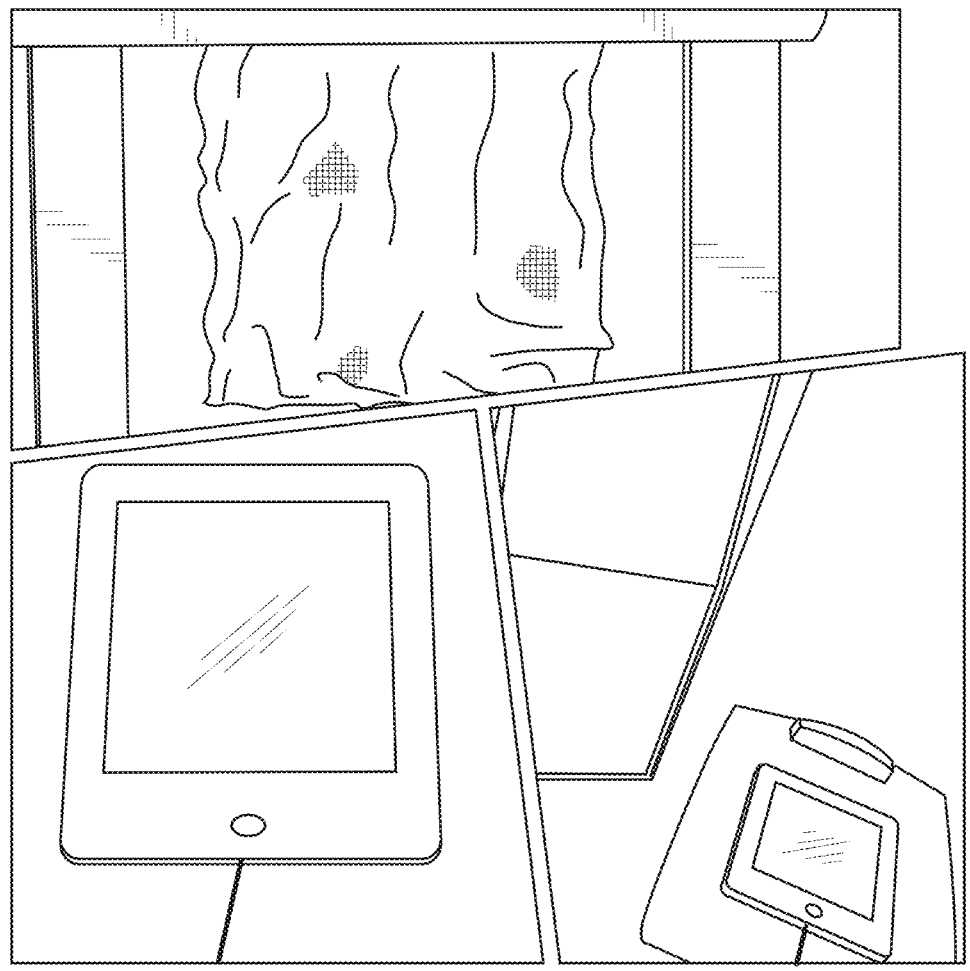
FIG. 1 depicts a Hathback and Chemiluminescence device.

The present invention relates to the unexpected discovery that administering a liquid nitric oxide releasing solution (NORS) to a subject provides a mechanism for delivering an effective amount of the gaseous NO (gNO) to one or both of the sites of administration, or to a targeted treatment site that is distal to the administration site. For example, administration of a liquid NORS intranasally provides gNO locally to a subject while allowing for targeted delivery of gNO to a different location in the distal airways or the lung of the subject. Further, the present invention relates to the unexpected discovery that administration of a liquid NORS provides for the quick delivery of the liquid NORS to the targeted treatment site, followed by an extended and prolonged release of gNO at the treatment site. The present invention is particularly suited to field or mobile applications, where time and space are limited. For example, the present invention is well suited for use with an ambulatory patient or subject whereby a patient's wound can be covered with a gauze soaked in NORS, covered with a gas impermeable bandage and sent home while they are continued to be treated with gNO for another 24 hours.

Accordingly, in one aspect of the invention, the NORS provides an extended release of gNO. In another aspect of the invention, the NORS is comprised of a low concentration of a nitric oxide releasing compound and/or a low amount of an acidifying agent. The present invention also includes methods for the treatment of a wound in a subject in need thereof. The present invention also includes a method for reducing the presence of a bacterium, fungi, virus or other pathogen by administering a NORS. In one embodiment, the solution may be delivered to at least a portion of the upper respiratory tract of a human. In a further embodiment, the solution may be instilled on a dressing below a gas impermeable or semi-impermeable cover. In a further embodiment, the solution may be in an open container for soaking a limb with an infection or wound.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the term "modulate" is meant to refer to any change in biological state, i.e. increasing, decreasing, and the like.

As used herein, a "therapeutically effective amount" is an amount of a therapeutic composition sufficient to provide a beneficial effect to a subject to which the composition is administered.

The terms "patient," "subject" and "individual" are interchangeably used to mean a warm-blooded animal, such as a mammal, suffering from a disease or disorder. It is understood that humans and animals are included within the scope of the term "subject," "subject" or "individual."

As used herein, the terms "treatment site" and "site of treatment" are used to mean an area, a region or a site on, or inside the body of, a subject, including a tissue, a wound, a lesion, an abscess, including intact skin. The treatment sites that can be treated by the methods of the invention include any area, region or site on the surface of, or inside the body of, a subject that can be exposed to gaseous nitric oxide. By way of nonlimiting examples, regions and sites that can be treated by the methods of the invention include, but are not limited to, external tissues (e.g. skin, etc.), internal tissues (e.g. mucosa, muscle, fascia, etc.), and internal organs (e.g. lungs, liver, etc.). It should be understood that many areas, regions and sites that are normally not amenable to exposure to gaseous nitric oxide can become amenable to exposure to gaseous nitric oxide after a wound, such as, for example, a surgical incision or traumatic laceration, is introduced to the body of a subject. Moreover, "treatment site" should not be construed to include only those areas, regions or sites that exhibit overt evidence of pathology, but rather should also be construed to include areas, regions or sites that may be asymptomatic, i.e., that do not contain overt evidence of pathology, but that may be affected nonetheless and that could, in time, exhibit more overt evidence of pathology. By way of nonlimiting examples, such a site can include a trauma wound, surgical wound, intact tissue or burn, including those that have come into contact with, or which is at risk of potentially coming into contact with, a pathogen that can colonize or infect the wound, and can be treated, or prophylactically treated, with the devices and methods of the invention.

"NORS" as used herein may refer to a nitric oxide releasing solution or substance.

A "disease" is a state of health of a subject wherein the subject cannot maintain homeostasis, and wherein if the disease is not ameliorated then the subject's health continues to deteriorate.

In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

A disease or disorder is "alleviated" if the severity of a symptom of the disease or disorder, the frequency with which such a symptom is experienced by a patient, or both, is reduced.

The term "treat" or "treatment," as used herein, refers to the alleviation (i.e., "diminution") and/or the elimination of a sign or symptom or a source of a sign or symptom of a disease or disorder. By way of several non-limiting examples, a symptom of a bacterial infection can be treated by alleviating a symptom of that disorder. A symptom of a bacterial infection can also be treated by altogether eliminating a symptom of that disorder. A bacterial infection or colonization can be treated by alleviating the source, or "cause," of that disorder. A bacterial infection or colonization can also be treated by eliminating the source of that disorder.

As used herein, an "antibiotic-resistant bacterium," is a bacterium that is a member of a species of bacteria that has historically exhibited greater susceptibility to one or more particular antibiotic agents than the antibiotic-resistant member bacterium presently exhibits.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

As mentioned previously, the present invention relates to systems and methods for administering a liquid NORS to a subject as a vehicle for releasing an effective amount of gNO to the site of administration and/or to a targeted treatment site that is distal to the administration site. Administration of the liquid NORS provides for the quick delivery of the liquid NORS to the targeted treatment site, followed by an extended and prolonged release of gNO at the treatment site.

The present invention provides a number of advantages over currently used NO treatments. For example, as presented herein, it has been unexpectedly found that the NORS of the present invention are capable of releasing a therapeutically effective amount of NO for an extended period of time while using a lower amount of one or both of a nitrite component and an acidifying agent than compositions of the prior art. Also as presented herein, it has been unexpectedly found that when the compositions of the instant invention are formulated as a liquid rather than as a cream or lotion, a surprising and significantly more effective administration of gNO is achieved, including a longer duration of gNO release and therefore the ability to use of a reduced amount or dosage of the composition. Moreover, unlike topical applications which are applied directly to the lesion and therefore have an area of treatment limited to only the site of application, gNO released from a liquid NORS can also treat lesions or microbes that are not at the site of application. For example, the liquid NORS can be sprayed into the nostrils of the subject, resulting in the extended release of gNO into the subject's inspired air stream over minutes to hours. Furthermore, the duration of treatment can be reduced to a single treatment versus multiple treatments over weeks to months, such as when a topical application is used.

In one aspect, the present invention provides methods and compositions useful for the treatment of diseases and disorders where nitric oxide delivery is beneficial. In one embodiment, the methods and compositions of the present invention are useful for the treatment of a wound in a subject in need thereof. In one embodiment, the method further comprises covering the wound with a gas impermeable cover. In another embodiment, the methods and composition are useful for treating fungal or diabetic associated infections of the feet. It should be appreciated that the NORS of the present invention may be suitable for treating any infection caused by a microorganism or pathogen, including a bacterium, a virus, a fungus, a protozoan, a parasite, an arthropod, and the like.

NO Releasing Solutions

The NORSs of the present invention provide an extended release of gNO to a subject in need thereof. By "extended release," it is meant that an effective amount of NO gas is released from the formulation at a controlled rate such that therapeutically beneficial levels (but below toxic levels) of the component are maintained over an extended period of time ranging from, e.g., about 5 seconds to about 24 hours, thus, providing, for example, a 30 to 60 minute, or several hour, dosage form. In one embodiment, the NO gas is released over a period of at least 30 minutes. In another embodiment, the NO gas is released over a period of at least 8 hours. In another embodiment, the NO gas is released over a period of at least 12 hours. In another embodiment, the NO gas is released over a period of at least 24 hours. An extended release NORS is beneficial in that the solution can be administered to the subject over a short period of time, while the release of NO from the solution continues following administration. Moreover, the use of an extended release NORS allows the subject to remain ambulatory following administration of the solution, as opposed to remaining stationary while being connected to a NO-releasing device in order to receive treatment.

In one aspect, the NORSs of the present invention have antibacterial, antifungal, and/or antiviral properties, and therefore may be useful as antibacterial, antifungal, and/or antiviral agents. In one embodiment, the NORS is an antibacterial agent effective against *Acinetobacter baumanii*. In another embodiment, the NORS is an antibacterial agent effective against Methicillin-resistant *Staphylococcus aureus*. In another embodiment, the NORS is an antibacterial effective against *Escherichia coli*. In one embodiment, the NORS is an antifungal agent effective against *Trichophyton rubrum*. In another embodiment, the NORS is an antiviral agent effective against Influenza H1N1.

The solution of the present invention becomes active when the nitrites and acids mix in saline or water in which the pH of the solution is below 4.0 and exhibits an increased or enhanced production level of nitric oxide gas over an extended period of time. In one embodiment, the pH of the active state of the nitric oxide releasing solution is between a pH of about 1.0 and a pH of about 4.0. In another embodiment, the pH of the active state of the nitric oxide releasing solution is between a pH of about 3.0 and a pH of about 4.0. In one embodiment, the pH is about 3.2. In another embodiment, the pH is about 3.6. In another embodiment, the pH is about 3.7. In one embodiment, the pH is about 4.0. In another embodiment, the pH is below about 4.0. Because the nitric oxide releasing solution of the present invention is not active until the acid interacts with the nitrites in liquid, the nitrite solution can be pre-made, transported and set up for administration while in its dormant state (pH greater than 4.0), without producing any appreciable nitric oxide gas or without losing its ability to produce an effective amount of nitric oxide gas. Then, when a user is ready to deliver or administer the solution for treatment of a human subject, the solution can be activated immediately prior to administration to the human subject by the addition of an acid (pH driven below 4.0), thereby maximizing the amount of nitric oxide gas produced by the administered dosage of solution.

In one embodiment, the pH of the solution can be lowered via addition of at least one acidifying agent into the solution. Introduction of the acidifying agent drives the solution reaction towards the reactants, thus reducing the pH (creating more acid), which in turn creates more nitric oxide gas.

For example, by introducing sodium nitrite (or other salts of nitrites) to a saline solution it will very slowly produce nitric oxide gas, but in an undetectable amount (as measured by chemiluminescence analysis methodology (ppb sensitivity)). The rate of NO produced from the solution increases as the pH is decreased, particularly as it drops below pH 4.0. NO is produced based on the following equilibrium equations:

$$NO_2^- + H^+ \rightarrow HNO_2 \qquad 1$$

$$2HNO_2 \rightarrow N_2O_3 + H_2O \rightarrow H_2O + NO + NO_2 \qquad 2a$$

$$3HNO_2 \rightleftharpoons 2NO + NO_3^- + H_2O + H^+ \qquad 2b$$

Therefore, an acidifying agent, for example an acid, may donate the $H^+$ to the nitrite ($NO_2^-$). The more $H^+$ present, the faster the reaction will go towards $HNO_2$ and the more NO will be produced.

In one embodiment, the nitric oxide releasing solution includes the use of a water- or saline-based solution and at least one nitric oxide releasing compound, such as nitrite or a salt thereof. In one embodiment, the solution is a saline-based solution. In one embodiment, the nitric oxide releasing compound is a nitrite, a salt thereof, and any combinations thereof. Non-limiting examples of nitrites include salts of nitrite such as sodium nitrite, potassium nitrite, barium nitrite, and calcium nitrite, mixed salts of nitrite such as nitrite orotate, and nitrite esters such as amyl nitrite. In one embodiment, the nitric oxide releasing compound is selected from the group consisting of sodium nitrite and potassium nitrite, and any combinations thereof. In another embodiment, the nitric oxide releasing compound is sodium nitrite. In one embodiment, the solution is comprised of sodium nitrite in a saline solution. In another embodiment, the solution is comprised of potassium nitrite in a saline solution.

In one embodiment, the concentration of nitrites in the solution is between 0.07% w/v and about 0.5% w/v. In one embodiment, the concentration of nitrites in the solution is no greater than about 0.5% w/v. In another embodiment, the concentration of nitrites in the solution is about 0.41% w/v. In another embodiment, the concentration of nitrites in the solution is between about 0.07-0.5% w/v. As used herein, the term "w/v" refers to the (weight of solute/volume of solution)×100%.

The solution of the present invention may also contain at least one acidifying agent. As described elsewhere here, the addition of at least one acidifying agent to the solution of the present invention contributes toward increased production of NO. Any acidifying agent which provides increased production of NO is contemplated by the present invention. In one embodiment, the acidifying agent is an acid. Non-limiting examples of acids include ascorbic acid, ascorbyl palmitate, salicylic acid, malic acid, lactic acid, citric acid, formic acid, benzoic acid, tartaric acid, hydrochloric acid, sulfuric acid, and phosphoric acid. In one embodiment, the acid is selected from the group consisting of ascorbic acid, citric acid, malic acid, hydrochloric acid, and sulfuric acid, and any combinations thereof. In one embodiment, the acid is citric acid.

As described above, the amount of acidifying agent present in the solution will directly affect the rate of the reaction to produce NO. In one embodiment, the amount of acidifying agent is no greater than about 0.5% w/v. In another embodiment, the amount of acidifying agent is about 0.5% w/v. In another embodiment, the amount of acidifying agent is about 0.2% w/v. In one embodiment, the amount of acidifying agent is about 0.07% w/v. In another embodiment, the amount of acidifying agent is between about 0.07-0.5% w/v.

The solution may be administered to the subject as an extended release formulation of NO gas, and optionally with a carrier formulation, such as microspheres, microcapsules, liposomes, etc., as a topical ointment or solution, or in an intranasal injection, as known to one skilled in the art to treat a microbial disease or disorder.

The solution of the present invention may release a therapeutically effective concentration of NO. In one embodiment, the therapeutically effective concentration of NO is between about 100 ppm and about 1000 ppm. In another embodiment, the therapeutically effective concentration of NO is between about 120 ppm and about 400 ppm. In a preferred embodiment, the therapeutically effective concentration of NO is about 160 ppm.

Methods

The present invention provides a method of treating a subject in need comprising the delivery of a nitric oxide releasing solution to a treatment site of the subject. The present method can be used to treat, prevent, or reduce the incidence of any disease, disorder, or condition where nitric oxide delivery is beneficial. Exemplary diseases, disorders, or conditions, include but are not limited to, respiratory diseases, respiratory infections, wounds, burns, topical infections, inflammatory diseases, and the like. In a preferred embodiment, the disease, disorder or condition is foot fungus. In another preferred embodiment, the disease, disorder or condition is diabetic foot ulcers. In another preferred embodiment, the disease, disorder or condition is infected surgical wounds.

The present invention is unique in that it allows for delivery of nitric oxide to an ambulatory subject, or to an assembly line of subjects where the administration protocol for delivery of the NORS is accomplished in a short time period. This is particularly important and valuable when treating humans, in that a patient need be only momentarily situated for the short period of administration, and then can move about or be moved, as desired. For example, the extended release and delivery of nitric oxide to the treatment site by way of the administered nitric oxide releasing solution allows for the treated subject to remain ambulatory during treatment, or stationary for a very short period of time. Thus, the subject is not constrained to a nitric oxide delivery device during the entire duration of nitric oxide delivery. Rather, the NORS can be administered to the subject over a short duration of treatment, and following administration the NORS will continue to deliver an extended release of a therapeutically effective amount of nitric oxide to the subject. In a preferred embodiment, the subject is a human.

In one aspect, the present invention includes a method for the treatment of a wound in a subject in need thereof. In one embodiment, the method of the present invention comprises spraying the wound of a subject with a nitric oxide releasing solution that has been prepared just prior to application and then covered with a gas impermeable or semi-impermeably cover that will retain the produced nitric oxide under the cover and therefore expose the wound to the therapeutic concentration of nitric oxide for an extended period of time. The cover may have a small bleed hole to control or limit the pressure under the cover. This allows the subject to be treated and then be ambulatory, eliminating the need for the subject to remain next to the gas source.

In one embodiment, the method comprises the treatment of a wound, including but not limited to, an open wound, cut, scrape, burn, abscess, lesion, surgical wound, trauma wound, disease-associated wound or the like. In certain embodiments, the method comprises administering the dormant solution to the treatment site. In certain embodiments, the acidifying agent is added to the dormant solution which lowers the pH of the dormant solution thereby creating the nitric oxide releasing solution. For example, in one embodiment, the nitric oxide releasing solution is produced by adding the acidifying agent to the dormant solution directly on the treatment site. In another embodiment, the nitric oxide solution is produced away from the treatment site, and is then topically applied to the treatment site. In one embodiment, the method comprises administering a gas impermeable cover over the treatment area of the subject, in order to constrain the produced nitric oxide gas over the treatment site. The cover may be applied prior to, during, or after administration of the dormant solution or nitric oxide releasing solution. The nitric oxide releasing solution provides for extended nitric oxide production, thereby providing continuous delivery of therapeutic nitric oxide to the wound of the subject.

Patients with open wounds resulting from physical injury or infection or from the result of known diseases such as diabetes or venous stasis disease, have the need to have their wounds treated with a nitric oxide gas or nitric oxide compound. Because the NORSs of the present invention provide an extended release of nitric oxide, and thus require a short duration of time for administration of the solution, subjects treated with an NORS of the present invention can remain ambulatory following administration of the solution. Therefore, the present invention is advantageous over prior methods, where patients being treated with nitric oxide gas are required to remain stationary in a location where the delivery device and high pressure gas source are connected to their wound.

In one embodiment, the present invention provides a method of treating skin inflammation, including inflammation associated with psoriasis, dermatitis (atopic, contact, sebborheic, etc), eczema, tinea pedis, and rosacea. In certain embodiments, the method comprises administering the dormant solution to the treatment site. In certain embodiments, the acidifying agent is delivered to the dormant solution which lowers the pH of the dormant solution thereby creating the nitric oxide releasing solution. For example, in one embodiment, the nitric oxide releasing solution is produced by applying an acidifying agent to the dormant solution directly on the treatment site. In another embodiment, the nitric oxide solution is produced away from the treatment site, and is then topically applied to the treatment site. In one embodiment, the method comprises administering a gas impermeable cover over the treatment area of the subject, in order to constrain the produced nitric oxide gas over the treatment site. The cover may be applied prior to, during, or after administration of the dormant solution or nitric oxide releasing solution. The nitric oxide releasing solution provides for extended nitric oxide production, thereby providing continuous delivery of therapeutic nitric oxide to the treatment site of the subject.

In certain embodiments, the nitric oxide releasing solution is prepared just prior to administration to the subject through the administration of an acidifying agent to a dormant solution. For example, as described elsewhere herein, administration of the acidifying agent to the dormant solution results in the lowering of the pH of the dormant solution, thereby activating the nitric oxide releasing solution to be administered to the treatment site. Importantly, the nitric oxide releasing solution provides for extended production of nitric oxide. In one embodiment, the nitric oxide releasing solution produces nitric oxide for a period of between 1 minute and 24 hours. In one embodiment, the nitric oxide releasing solution produces nitric oxide for a period of between 10 and 45 minutes. In one embodiment, the nitric oxide releasing solution produces nitric oxide for at least 15 minutes. In one embodiment, the nitric oxide releasing solution produces nitric oxide for at least 30 minutes. In another embodiment, the nitric oxide releasing solution produces nitric oxide for at least 1 hour. In another embodiment, the nitric oxide releasing solution produces nitric oxide for at least 4 hours. In another embodiment, the nitric oxide releasing solution produces nitric oxide for at least 8 hours. In another embodiment, the nitric oxide releasing solution produces nitric oxide for at least 12 hours. In another embodiment, the nitric oxide releasing solution produces nitric oxide for at least 24 hours. Thus, the administered nitric oxide releasing solution provides for continuous delivery of nitric oxide to the treatment site of the subject.

The nitric oxide releasing solution may be administered to the subject in a variety of forms. The nitric oxide releasing solution may be administered as a liquid, a spray, a vapor, micro-droplets, mist, footbath or any form which provides the release of nitric oxide from the solution, as would be understood by one skilled in the art. In one embodiment, the nitric oxide releasing solution is administered as a spray. In another embodiment, the nitric oxide releasing solution is administered as a vapor. The amount or dosing volume of administered nitric oxide releasing solution may be varied in order to optimize the duration of nitric oxide production and delivery. In one embodiment, the amount of nitric oxide releasing solution administered to a subject is between about 0.1 mL and 5000 mL. In another embodiment, the amount of nitric oxide releasing solution administered to a subject is between about 10 mL and 1000 mL. In one embodiment, the amount of nitric oxide releasing solution administered to a subject is about 2 mL. In one embodiment, the amount of nitric oxide releasing solution administered to a subject is about 10 mL. In one embodiment, the amount of nitric oxide releasing solution administered to a subject is about 32 mL. In another embodiment, the amount of nitric oxide releasing solution administered to a subject is about 160 mL. The nitric oxide releasing solution may be readministered one or more times, as necessary to effectively treat the subject. In one embodiment, the nitric oxide releasing solution is administered once to a subject. In another embodiment, the nitric oxide releasing solution is administered multiple times to a subject, where the NORS is readministered substantially after completion of the extended release of gNO from the prior dosage administered.

In certain embodiments, nitric oxide releasing solution is directly administered into the upper respiratory tract of the subject. For example, in one embodiment, the nitric oxide releasing solution is sprayed into the upper respiratory tract of the subject. The solution may be administered into the upper respiratory tract of the subject once an hour, once a day, once a week, once every two weeks, once a month, once every two months, once a year, and any and all ranges therebetween as required to treat the subject. In one embodiment, the solution is sprayed once a week. In another embodiment, the solution is sprayed once a week for four consecutive weeks. The nitric oxide releasing solution provides for extended nitric oxide production, thereby providing continuous delivery of therapeutic nitric oxide to the upper respiratory infection of the subject.

The duration of administering the nitric oxide releasing solution to the subject may be varied in order to optimize delivery. In one embodiment, the nitric oxide releasing solution is administered to the subject over a time period of less than 5 seconds. In another embodiment, the nitric oxide releasing solution is administered to the subject over a time period of about 5 seconds. In another embodiment, the nitric oxide releasing solution is administered to the subject over a time period of about 30 seconds. In another embodiment, the nitric oxide releasing solution is administered to the subject over a time period of about 1 minute. In another embodiment, the nitric oxide releasing solution is administered to the subject over a time period of about 2 minutes. In another embodiment, the nitric oxide releasing solution is administered to the subject over a time period of about 10 minutes. In another embodiment, the nitric oxide releasing solution is administered to the subject over a time period of about 30 minutes.

In one embodiment, the method comprises the treatment, prevention, or reduction of incidence of a respiratory disease or disorder in a subject. Exemplary respiratory diseases or disorders treated by way of the present method include, but are not limited to emphysema, chronic bronchitis, asthma, adult respiratory syndrome (ARDS), chronic obstructive pulmonary disease (COPD), cystic fibrosis, influenza, and the like. In certain embodiments, the method comprises the treatment of a respiratory disease or disorder caused by a bacterial, fungal or viral infection. In some embodiments, the infection is caused by a bacterium. In other embodiments, the infection is caused by a virus. Treatment of a respiratory disease by way of the present invention comprises the delivery of a nitric oxide releasing solution into the upper respiratory tract of the subject to be treated. For example, in certain embodiments, the nitric oxide releasing solution may be injected, sprayed, inhaled, or instilled into the respiratory tract of the subject. The nitric oxide releasing solution may be administered to the respiratory tract of the subject via the nasal cavity or oral cavity of the subject. In one embodiment, the nitric oxide releasing solution is sprayed into the upper respiratory tract of the subject. In one embodiment, the solution is administered to the subject intranasally. In one embodiment, the solution is administered to the sinuses. The nitric oxide releasing solution provides for extended nitric oxide production, thereby providing continuous delivery of therapeutic nitric oxide to the upper respiratory tract of the subject.

In one embodiment, the method comprises the treatment of a wound, including but not limited to, an open wound, cut, scrape, burn, abscess, lesion, surgical wound, trauma wound, disease-associated wound wherein the wound is caused by or affected by an infection. For example, the infection may be caused by a fungus or a bacterium, including a bacterium that has developed resistance to one or more antibiotics. In one embodiment, the bacterium is *S. aureus*.

In one embodiment, the method comprises the treatment, prevention, or reduction of incidence of a respiratory disease or disorder in a subject, wherein the disease or disorder is caused by an infection. For example, the infection may be caused by a virus, a fungus, a protozoan, a parasite, an arthropod or a bacterium, including a bacterium that has developed resistance to one or more antibiotics. In some embodiments, the infection is caused by a bacterium. In other embodiments, the infection is caused by a virus.

In one embodiment, the method comprises the treatment, prevention, or reduction of incidence of an infection in a subject, including infections caused by a virus, a fungus, a protozoan, a parasite, an arthropod or a bacterium, including a bacterium that has developed resistance to one or more antibiotics. In some embodiments, the infection is caused by a bacterium. In one embodiment, the bacterium is *Acetobacter baumanii*. In another embodiment, the bacterium is Methicillin-resistant *Staphylococcus aureus*. In another embodiment, the bacterium is *Escherichia coli*. In other embodiments, the infection is caused by a virus. In one embodiment, the virus is Influenza H1N1. In other embodiments, the infection is caused by a fungus. In one embodiment, the fungus is *Trichophyton Rubrum*.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein. Unless otherwise specified, the NORS as described in the following experiments is a saline based solution having a citric acid concentration of about 0.2% and sodium nitrite concentration of about 0.41% (60 mM).

Example 1: Extended Release of NO from NORS

The materials and methods employed in these experiments are now described.

A NORS solution was prepared at a nitrite strength of 0.3% w/v and pH 3.7. Once ready, a 3×3 in gauze was dipped into the solution, lightly squeezed to discard excess liquid and placed in a "Hath Bath" device (FIG. 1). At different time points, the NO that was being released was measured with a chemiluminescence analyzer (NOA 280i, General Electric, CO).

The results of the experiments are now described.

Figure 2A:
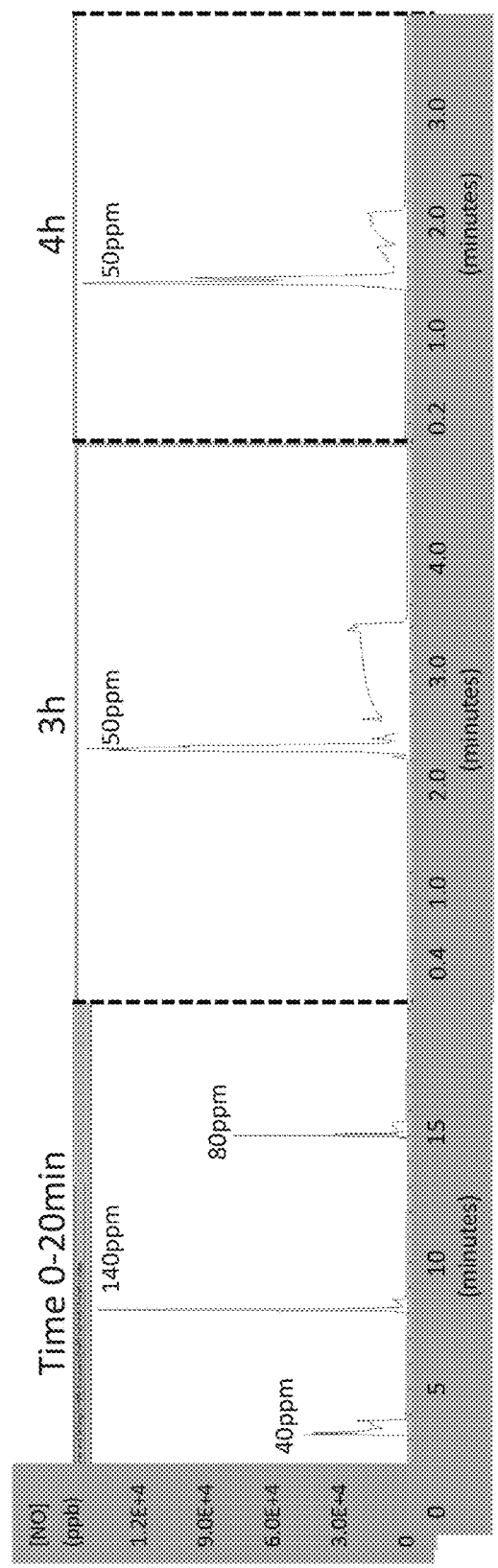
FIG. 2A depicts the amount of NO detected at 3, 8, and 15 min as well as 3 and 4 hours.
Figure 2B:
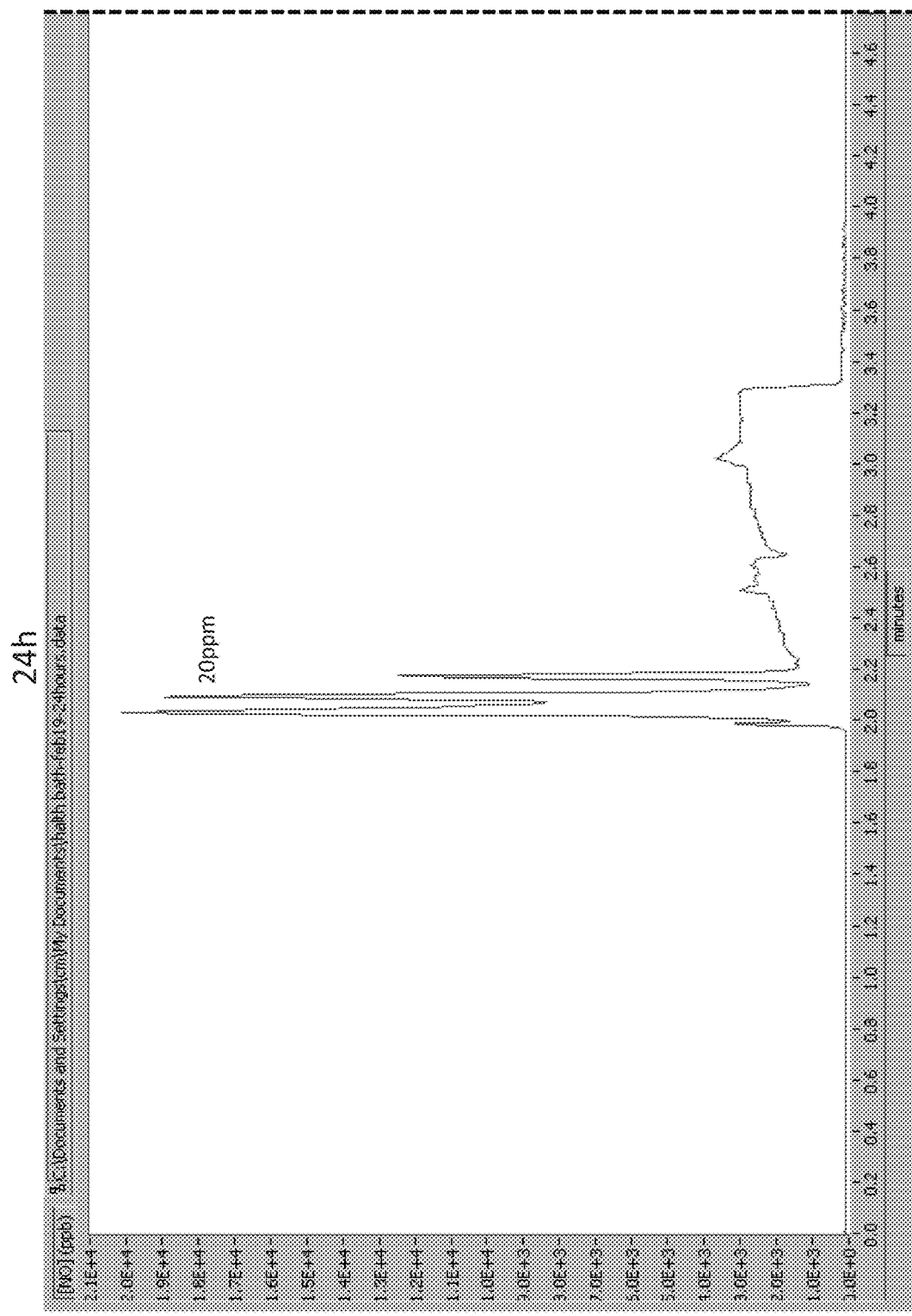
FIG. 2B depicts the amount of NO detected at 24 hours. The X scale is TIME (minutes) from start on measuring point (showing pre-measuring amount as 0-0.1 ppm) and Y scale showing amount of NO (measured in ppb).

FIG. 2 shows the amount of NO detected at 3, 8, 15 min as well as 3, 4 (2A) and 24 (2B) hours. The X scale is TIME (minutes) from start on measuring point (showing pre-measuring amount as 0-0.1 ppm) and Y scale showing amount of NO (measured in ppb).

The Chemiluminescent analyzer has a sample draws rate of 200 cc per min and thus, there is an initial peak and reduction in NO concentration following that. The "Hathback" may not be completely sealed and thus some NO may "escape". However, release of NO was still detected 24 hours after gauze was saturated with the NORS solution.

Example 2: Antibacterial Efficacy of NORS on *Acetobacter baumanii*, Methicillin-Resistant *Staphylococcus aureus* and *Escherichia coli*

All of the following bacteria are common in wound infections:

*A. baumannii* is a species of pathogenic bacteria, referred to as an aerobic gram-negative bacterium, which is resistant to most antibiotics. Reported to cause infections among American soldiers wounded in Iraq.

*E. coli*—gram negative, common bacteria.

*S. aureus* is a common cause of surgical-site infection. It's a gram positive and it is frequently part of the skin flora.

Methicillin-Resistant *Staphylococcus aureus*—MRSA is, by definition, a *S. aureus* bacteria that has developed resistance to beta-lactam antibiotics which include the penicillins (methicillin, dicloxacillin, nafcillin, oxacillin, etc.) and the cephalosporins.

The materials and methods employed in these experiments are now described.

Bacterial Preparation

*A. baumanii*, MRSA and *E. coli* bacterial culture were obtained from American Type Culture Collection (ATCC #BAA-747, #700698 and #25922). Bacteria were grown in Lysogeny broth (LB) (*E. coli* and *A. baumanii*) or Brain-Heart Infusion Broth (BHI) (MRSA) to 0.5 McFarland standard. 1 mL aliquots of these preparation containing approximately $2.5 \times 10^8$ cfu/mL were stored at −70° C. On the day of the experiments the fresh stock was removed from the freezer, thawed, and 2 mL of LB or BHI was added. Cultures were further diluted with LB or BHI to $10^6$ colony forming units per milliliter (cfu/mL).

NORS Preparation and Testing Procedure

NORS was prepared by mixing a specific concentration of sodium nitrite (0.07-0.41%) in saline and then reducing the pH to 3.7 with citric acid. Controls were—saline, sodium nitrite at 0.41% and pH of 6, and saline at pH 3.7 (reduced with citric acid).

100 μl of bacteria ($10^6$ cfu/mL) was mixed with 900 μl NORS. After 10 min, samples were serially diluted and plated on either LB or BHI agar plates. Cultures were incubated at 37° C. overnight (O/N) and then cfus counted to quantify bacterial growth. Each experiment was done in triplicate and each experiment repeated three times.

The results of the experiments are now described.

Figure 3:
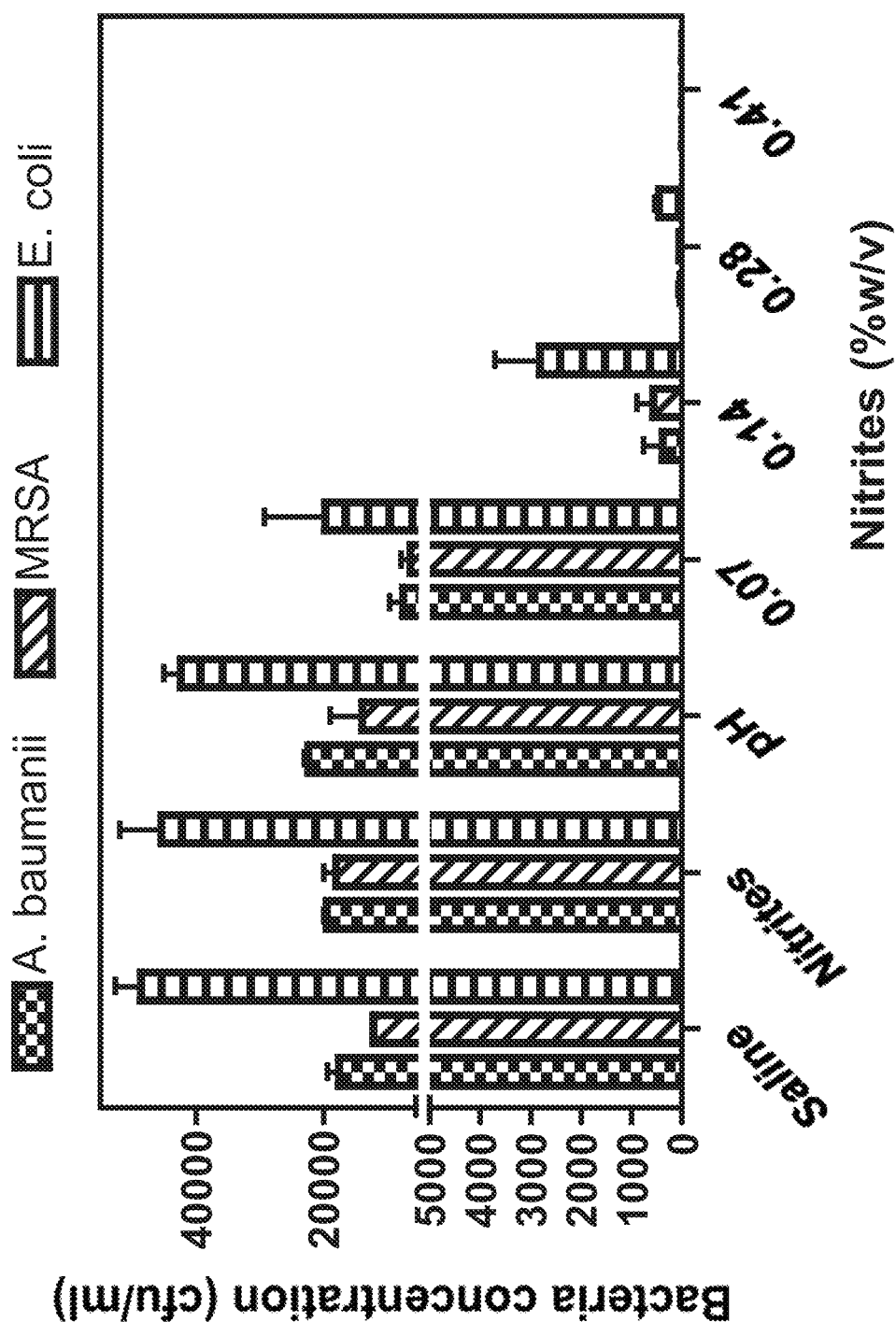
FIG. 3 is a graph depicting the antibacterial efficacy of NORS against *A. baumanii*, methicillin-resistant *S. aureus*, and *E. coli* using NORS of varying nitrite concentrations (0.07-0.41%) at pH 3.7. Controls were—saline, nitrites only at 0.41% (pH 6) and saline with reduced pH to 3.7. Error bars indicate standard deviation for three experiments with 3 repetitions each.
Figure 4:
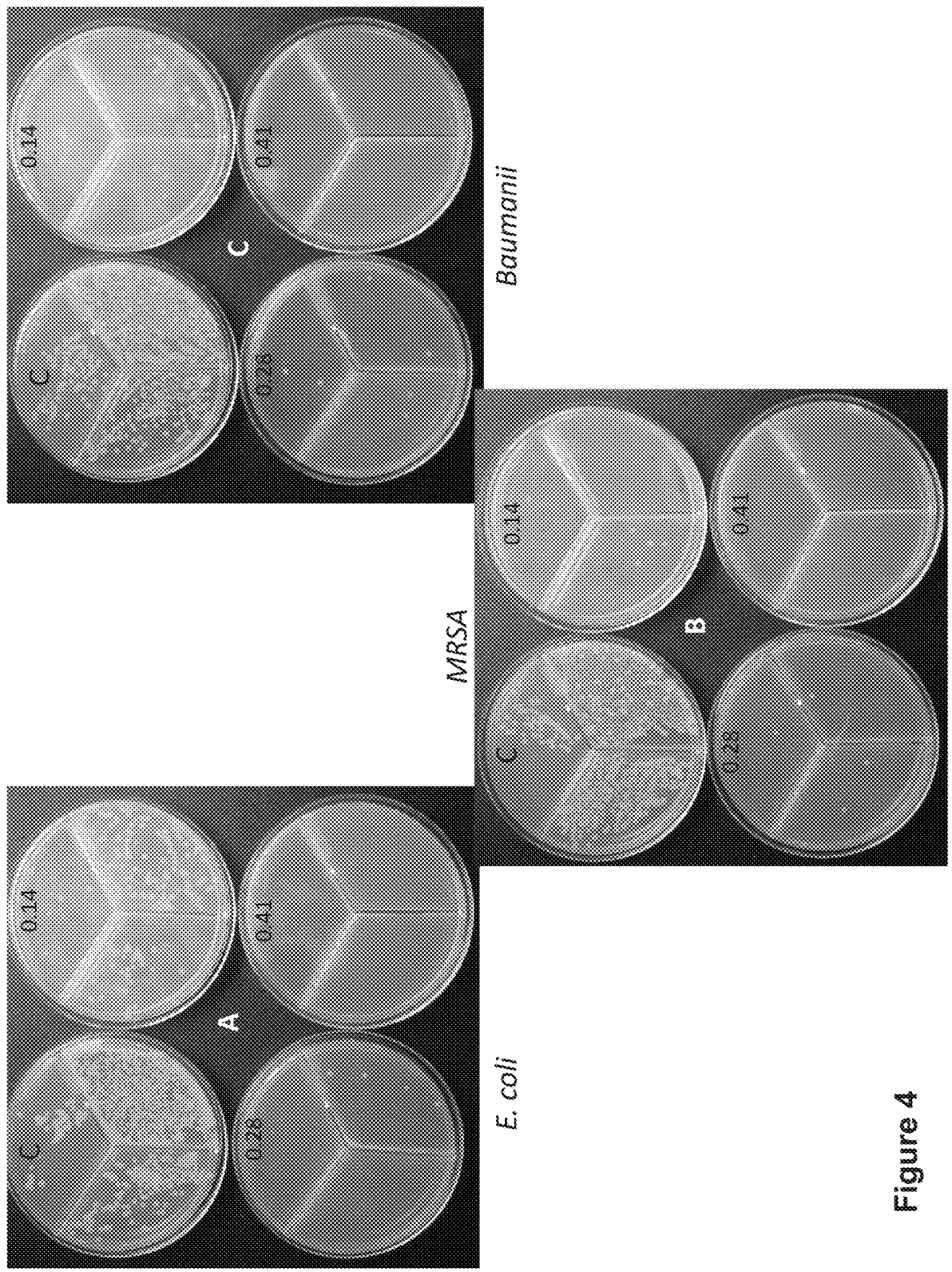
FIG. 4 depicts LA/BHI agar plates, plated with *A. baumanii*, methicillin-resistant *S. aureus*, and *E. coli* following 10 min exposure to NORS.

NORSs comprised of citric acid and each with a different concentration of nitrites in saline solution were tested on 3 different bacteria species (*A. baumanii*, MRSA and *E. coli*) at 10 min exposure time in order to evaluate antibacterial efficacy of the NORS. 0.41% nitrites at pH 3.7 (0.2% w/v citric acid) resulted in complete eradication of all three bacteria (FIGS. 3 and 4).

Example 3: Antibacterial Efficacy of NORS on *Mannheimia Haemolytica*

The main bacterial pathogen of BRDc is *M. haemolytica*, which produces a potent leukotoxin that is its principal virulence factor. In this study the effect of NORS on bacteria that is associated with bovine respiratory infections was tested to demonstrate the overall effectiveness of the present invention against diseases also found in other mammalian species.

The materials and methods employed in these experiments are now described.

Bacterial Preparation

*M. haemolytica* bacterial cultures were isolated and obtained from the Agriculture and Agri-Food Canada Research Centre (Lethbridge, Canada). Bacteria were grown to 0.5 McFarland standard. 1 mL aliquots of these preparations containing approximately $2.5 \times 10^8$ cfu/mL were stored at −80° C. On the day of the experiments the fresh stock was removed from the freezer, thawed, and 2 mL of BHI was added. Cultures were further diluted with BHI to achieve $OD_{600}$ of 0.1. Two different serotypes of *M. haemolytica* were used. These serotypes were originally isolated from bovine nasopharyngeal swabs, and subsequently confirmed by biochemical and polymerase chain reaction (PCR) assays as *M. haemolytica* (Klima et al., 2011, Vet. Microbiol. 149:390-398). They were serotyped in the laboratory, against reference sera, which was generated in rabbits.

Antibacterial Effect of NORS on *M. Haemolytica*

NORS at different strengths was tested for efficacy against *M. haemolytica* serotypes. Saline was used as control. NORS (900 μl) was added to separate 1.5 mL sterile Eppendorf tubes. One hundred pi of culture containing each serotype at $10^6$ CFU/mL ($OD_{600}$ 0.1) was then added to each tube and incubated for 30 seconds, 1, 2, 5 and 10 minutes. Following incubation, samples from each tube were serially diluted and were plated on both BHI and blood agar sheep plates. Plates were incubated at 37° C. overnight (O/N). Each experiment was done in triplicate and each experiment repeated three times.

The results of the experiments are now described.

Figure 5:
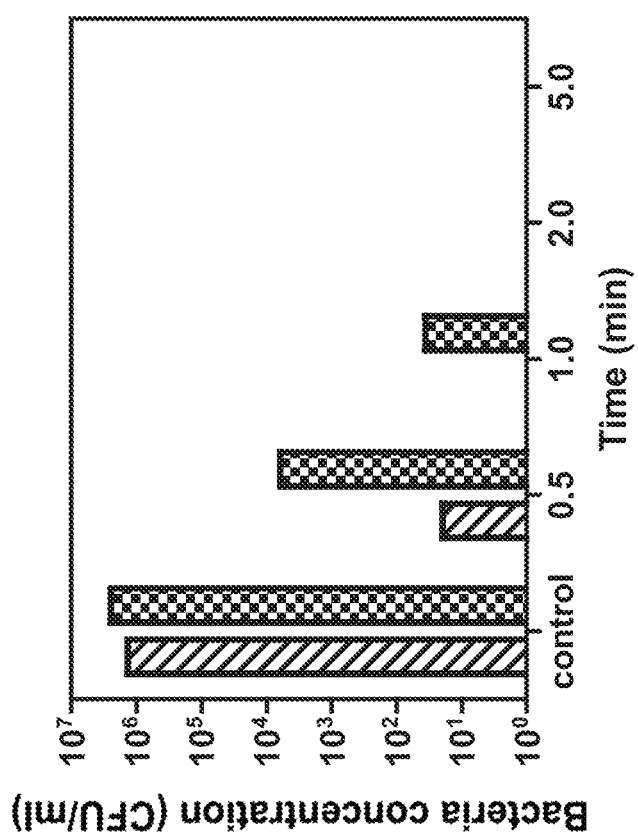
FIG. 5 is a graph depicting the viability of serotype 1 (stripes) and 6 (squares) of *M. haemolytica* after treatment with 0.41% NORS for 0.5, 1, 2, and 5 minutes. A star represents complete kill.

It was observed that using NORS, even for 0.5 min, resulted in significant ($P<0.05$) inhibition of *M. haemolytica*, compare to the control. Using NORS for 1 minute caused a complete eradication of one serotype of this bacteria and 2 minutes for both serotypes (FIG. 5). Both serotypes that were used here are isolates from feedlot cattle.

Example 4: Antiviral Efficacy of NORS on H1N1

For centuries influenza has affected human health both seasonally and with recurring pandemics. Despite significant reduction of disease burden through vaccination efforts, circulation of seasonal influenza A virus cause excess morbidity and mortality, particularly in patients with preexisting pulmonary conditions.

The materials and methods employed in these experiments are now described.
Cell Lines & Viruses Madin-Darby Canine Kidney Epithelial (MDCK) cells (ATCC CCL-34) were obtained from the American Type Culture Collection and maintained in Dulbecco minimal essential medium (DMEM) supplemented with 5% fetal bovine serum (FBS) and incubated at 37° C. in a humidified atmosphere with 5% $CO_2$ without antibiotics or antimycotic agents. MDCK cells were grown as monolayers in 75-$cm^2$ cell culture flasks. Passages between 3 and 15 were used for these experiments.

Viral strain was obtained from the laboratory stock from the British Columbia Center for Disease Control. Stocks of influenza A viruses, A/Denver/1/1957 (H1N1), were grown in MDCK for 48 hours, with medium containing 2 μg/mL modified trypsin (treated with TPCK) without serum. Stock virus was prepared as clarified cell-free supernatants. Virus concentration for stocks was determined by standard plaque assay on MDCK cells [27]. Virus titer for this stock was $6\times10^6$ plaque forming units (PFU)/mL respectively.
Experimental Protocol Aliquots of virus, diluted in phosphate buffer solution (PBS), usually 20 μL, were spotted onto the appropriate sterile glass surface, spread into a film by means of a sterile tip, and allowed to dry, within a biosafety cabinet (normally 15-20 min). Each sample received 2 sprays (100 μL) of different concentration of NORS (0.007-0.14% w/v) at pH 3.7. Controls consisted of equivalent samples sprayed with just saline, nitrites (0.14% at pH 6) and saline at pH 3.7. After 5 min, all samples, and equivalent control samples were reconstituted in 1.0 mL PBS and assayed by plaque formation (plaque forming units, pfu) in the appropriate cells.

The results of the experiments are now described.

Figure 6:
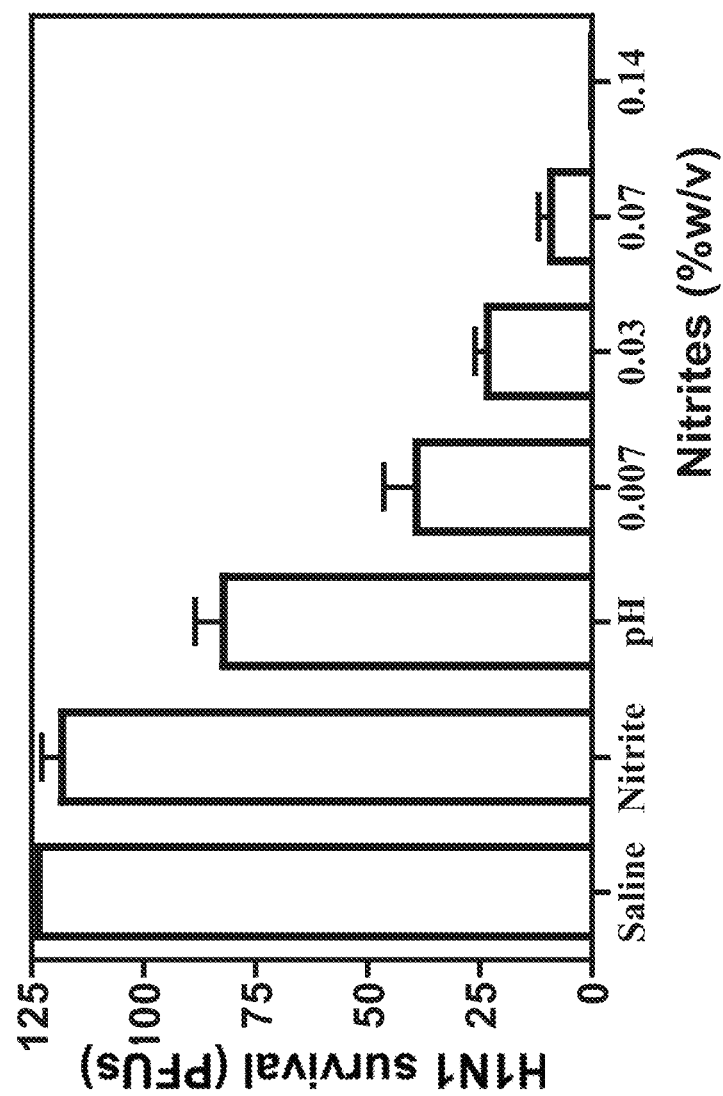
FIG. 6 is a graph depicting the antiviral efficacy of NORS against Influenza H1N1 using NORS of varying nitrite concentrations (0.007-0.14%) at pH 3.7. Controls were—saline, nitrites only at 0.14% (pH 6) and saline with reduced pH to 3.7. Error bars indicate standard deviation for three experiments with 3 repetitions each.
Figure 7B:
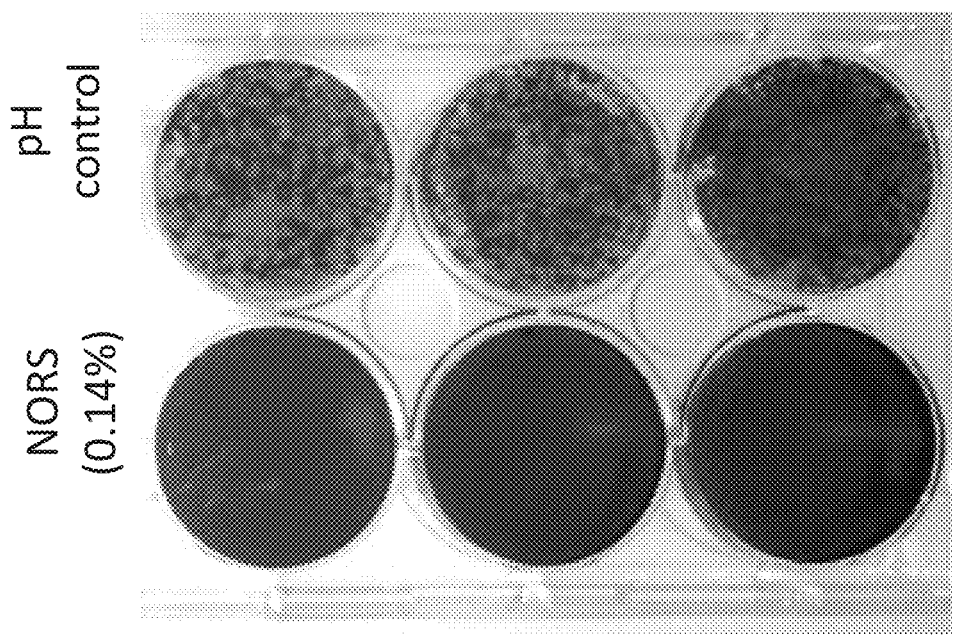
FIGS. 7A-7B are showing 2 photos of the plaque assay plates for A. saline control and NORS at 0.07% strength, B—pH control and NORS at 0.14% strength.
Figure 7A:
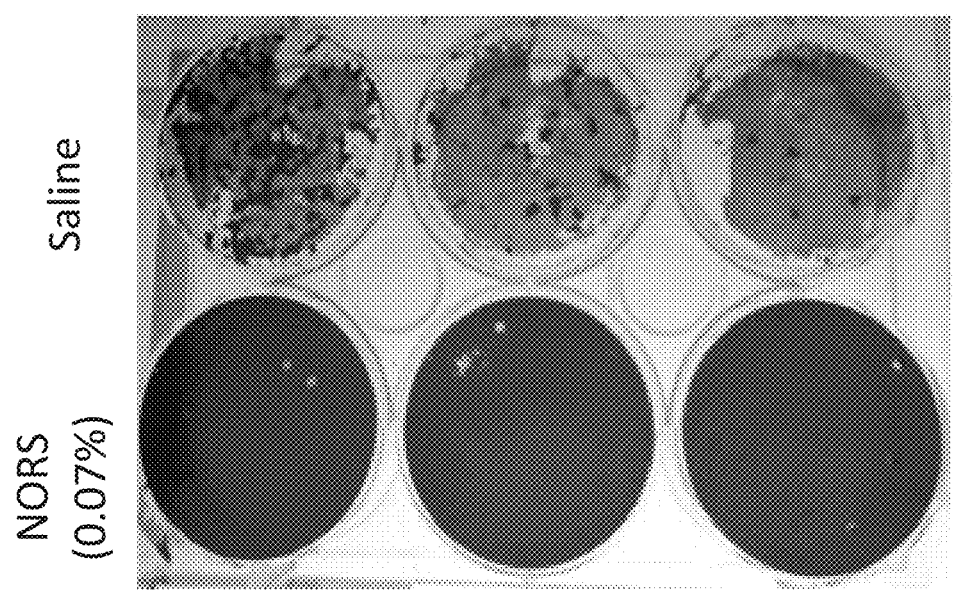

NORSs comprised of citric acid and each with a different concentration of nitrites in saline solution were tested on Influenza H1N1 in order to evaluate the antiviral efficacy of the NORS. A strength of 0.07% w/v nitrites at pH 3.7 (0.08% w/v citric acid) resulted in over 90% reduction (FIGS. 6 and 7A), while 0.14% caused complete eradication of the virus (FIGS. 6 and 7B).

Example 5: Antiviral Effect of NORS on Infectious Bovine Rhinotracheitis, Bovine Respiratory Syncytial Virus and Bovine Parainfluenza-3

It is clear that in cattle, as in humans and other mammalian species, an active viral infection dramatically increases susceptibility to contracting bacterial pneumonia (Bedling and Slifka, 2004). This has been demonstrated experimentally in cattle infected with any one of several bovine respiratory viruses such as bovine herpes virus 1 (BHV-1) or bovine respiratory syncytial virus (BRSV), after which renders cattle highly susceptible to a secondary bacterial infection when challenged with *M. haemolytica* (Hodgson et al., 2005; Yates 1982). These observations suggest that viral infection impairs host defense mechanisms against *M. haemolytica*, or amplifies undesirable aspects of the host response to this bacterial pathogen. In this example the effect of NORS on 3 viruses related to bovine respiratory infections was tested.

The materials and methods employed in these experiments are now described.
Cells and Viruses Madin-Darby bovine kidney (MDBK) cells (ATCC CCL 22) were grown in Eagle's minimum essential medium (MEM) containing 10% fetal bovine serum. Infectious Bovine Rhinotracheitis (IBR), Bovine Respiratory Syncytial Virus (BRSV) and Bovine parainfluenza-3 (PI-3) were used throughout the experiments. These viruses were propagated in MDBK cells in Dulbecco's modified Eagle's medium (DMEM) supplemented with 2% fetal bovine serum and stored at −80° C. until use. The amount of virus was measured by a plaque assay on MDBK cells.
Direct Virucidal Activity of NORS Virucidal activity was tested using equal volumes (0.025 mL) of virus suspension, containing $10^3$ to $10^7$ plaque-forming units (PFU/mL) of each of the 3 viruses and NORS. The two volumes were mixed together and incubated for 1 or 10 minutes at room temperature. The viruses were diluted with PBS containing 2% fetal bovine serum (FBS) and the number of infectious virus in each preparation was measured by a plaque assay.

The results of the experiments are now described.

IBR is the most susceptible virus to NORS, with a complete eradication with all initial titers after 10 min exposure and a significant (P<0.05) reduction for all titers after 1 min (FIG. 8A). PI3 was a bit less susceptible but significant reduction in viability at all titers was observed, both after 1 and 10 min (FIG. 8C). The least susceptible virus was BRSV, where no significant difference was observed after 1 min exposure, although a significant (P<0.05) reduction in viability was observed following 10 min exposure at all titers (FIG. 8B). The ability of NORS to eradicate the virus was found to be in direct correlation with the initial titer.

Example 6: Antifungal Efficacy of NORS

Most cutaneous infections are the work of the homogeneous group of keratinophilic fungi known as dermatophytes. Tinea pedis, known as Athlete's Foot, is the most prevalent form of superficial mycotic infections of the (Drake et al., 1996). Species from the genus *Trichophyton* are most commonly isolated from clinical samples, with *Trichophyton rubrum* and *Trichophyton mentagrophytes* being most common (Drake et al., 1996; Baran and Kaukhov, 2005).

Published paper-Regev-Shoshani et al., 2013, J. Appl. Microbio. 114:536-544

The materials and methods employed in these experiments are now described.
Fungal Preparation.

*Trichophyton rubrum* (18758) and *Trichophyton mentagrophytes* (114841) were obtained from the American Type Culture Collection (ATCC). Fungi were grown at 30° C. in Sabouraud Broth (SAB) for three days to a mycelial biomass of 1 mg/mL. Experiments on mycelial viability were done with this concentration. Conidia were isolated by shaking (on a Fisher shaker at 100 RPM) glass beads (Soda Lime 2 mm, VWR) for 60 seconds on the surface of mycelia grown on SAB agar plates for a minimum of seven days. Conidia covered glass beads were vortexed in sterile saline to suspend conidia in solution.

Preparation of NORS.

Nitric oxide releasing solutions (NORS) were prepared utilizing sodium nitrite and citric acid, as previously described. Specifically, this was done by dissolving solid sodium nitrite ($NaNO_2$) into sterile distilled water ($dH_2O$) to reach a final concentration of 0.007-0.14% w/v. Then, those solutions were acidified to pH 3.7 using a predetermined mass of citric acid (up to 0.1%).

NORS Antifungal Effect on Mycelial Viability of *T. rubrum* and *T. mentagrophytes*.

NORS containing $NaNO_2$ at concentrations of 0.007, 0.14, 0.35, 0.7% w/v were tested for their efficacy as antifungal agents. Sterile water (pH 6) was used as control. Sterile water adjusted to pH 3.7 using citric acid, and sterile water with 0.14% $NaNO_2$ (pH 6) were tested as well to determine whether either solution possessed a fungicidal effect by themselves. NORS (4 mL) was prepared and added to separate 5 mL sterile plastic tubes. One hundred µl of culture containing mycelia at a biomass of 1 mg/mL was then added to each tube and incubated for 10, 20 and 30 minutes. Following incubation, samples from each tube were serially diluted and were plated on SAB agar plates. Plates were incubated at 30° C. until growth could be detected and counted (about 3 days for *T. rubrum* and 2 days for *T. mentagrophytes*). Each experiment was done in triplicate and repeated three times.

A set of control experiments were done in order to eliminate the potential antifungal effect of the citric acid concentration in the treatment solution. Different concentrations of citric acid were prepared and pH was raised to 3.7 using NaOH. The same experimental methodologies with water as a control were used to perform these tests.

Gaseous Oxides of Nitrogen Produced from NORS and its Effect on Mycelial Growth.

The concentration of NO and other gases released from the NORS into the head space were determined by gas chromatography with a mass spectrometer detector (GC-MS). NORS (0.14% nitrites w/v) was prepared inside the sterile 5 mL plastic tubes described above. Each tube was then sealed for 30 minutes after which, 1 mL of the head space above the solution was analyzed by GC-MS. GC-MS (Varian™ CP-3800 Gas Chromatograph connected to a Varian™ 1200 Quadrupole MS) analysis was performed using a standard method that had previously been created and calibrated to separate and quantify NO, $NO_2$ and $N_2O$ molecules, using calibration gases. The method was set to a constant temperature of 31° C. with a sampling flow rate of 1 mL/min with helium gas as the carrier gas. Injector temperature was set to 120° C.

Figure 9:
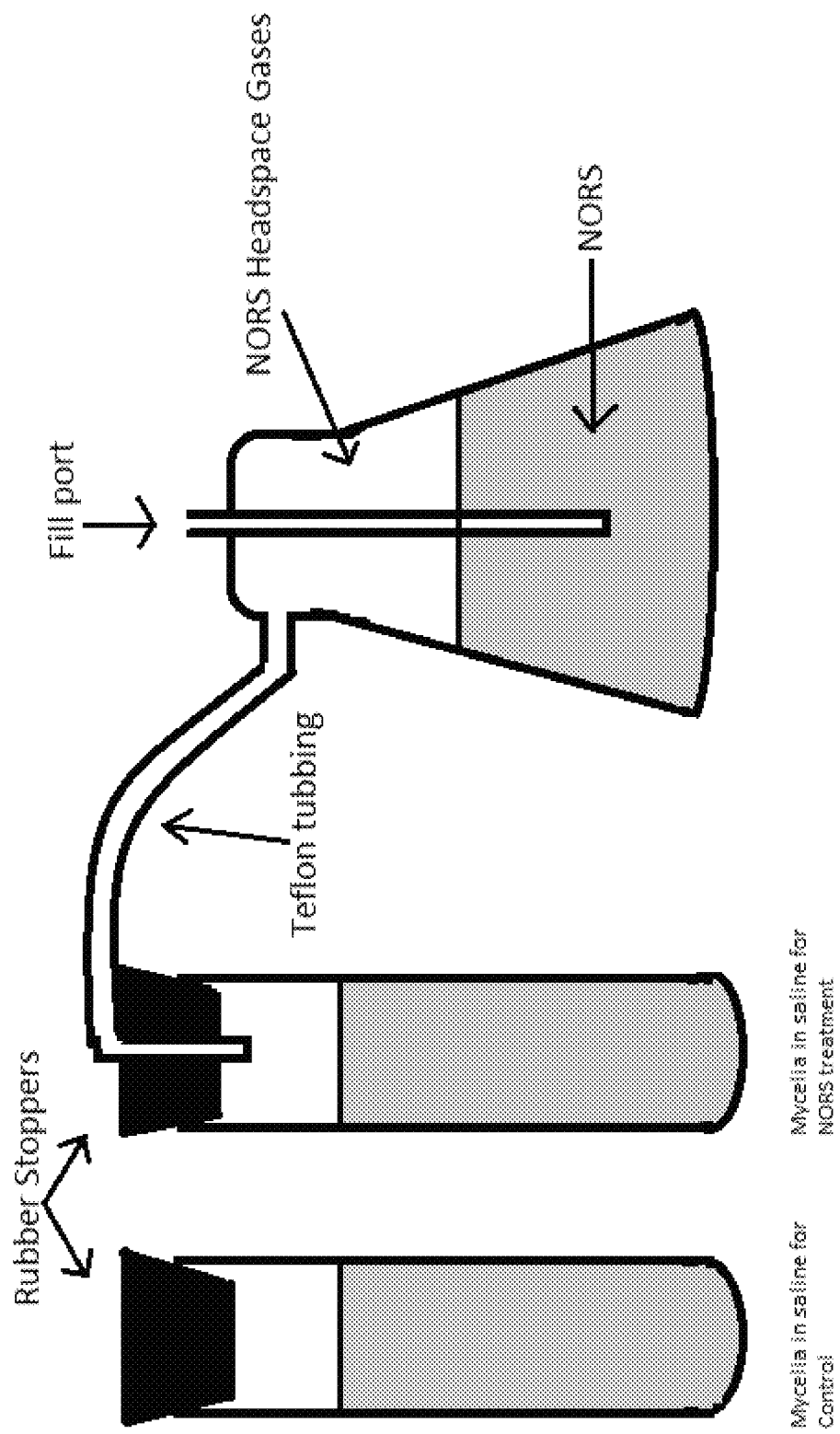
FIG. 9 is a schematic diagram of the apparatus constructed to test the effect of the head space gases generated by NORS on the mycelial growth.

In order to demonstrate that NO, found in the headspace, is responsible for the fungicidal effect of NORS, mycelia of *T. mentagrophytes* (10 mL at 1 mg/mL) were combined with 20 mL of sterile saline inside a sterile glass test tube connected via Teflon tubing to a separate glass apparatus, as illustrated in FIG. 9. Sterile saline (0.9% sodium chloride) was used in replacement of sterile $dH_2O$ in order to ensure any fungicidal activity measured was not the result of osmotic imbalances. NORS was added to the glass apparatus using a 50 mL syringe through the 'fill port' (FIG. 9) then sealed using paraffin laboratory film and plastic wrap. A higher strength NORS was required to produce a sufficient volume of gas to account for the much greater head space volume in the apparatus as opposed to the 5 mL tubes previously described. The apparatus was then left at room temperature for 2, 4, 8, 16 and 24 hours (each performed separately) after which, samples from the glass test tube were plated onto SAB agar plates, incubated at 30° C. for 48 hours and fungal viability determined. The growth from the exposed test tube was compared to a control of the same contents kept alongside the exposure in a sealed glass test tube (FIG. 9). Another control study was performed with the same apparatus, using saline instead of NORS. Nitrite concentration in the attached glass test tube was measured after each time point, using Griess reagent (Green et al. 1982).

The results of the experiments are now described.

NORS Antifungal Effect on Mycelial Viability of *T. rubrum* and *T. mentagrophytes*.

*T. rubrum* and *T. mentagrophytes* were grown from conidia for a minimum of 72 hours to a mycelial biomass of 1 mg/mL. Mycelia was added to treatment or control tubes and incubated for up to 30 minutes, after which, samples were plated and concentration (cfu/mL) was determined. As NORS is formulated from nitrites and citric acid (lowering pH to 3.7), the individual exposure effect of water at pH 3.7 and 0.14% w/v nitrites at pH 6 was tested and compared to an appropriate control. Minimal to no effect was detected after a 30 minute exposure with either 0.14% sodium nitrite (pH 6) or citric acid at pH 3.7.

Figure 10:
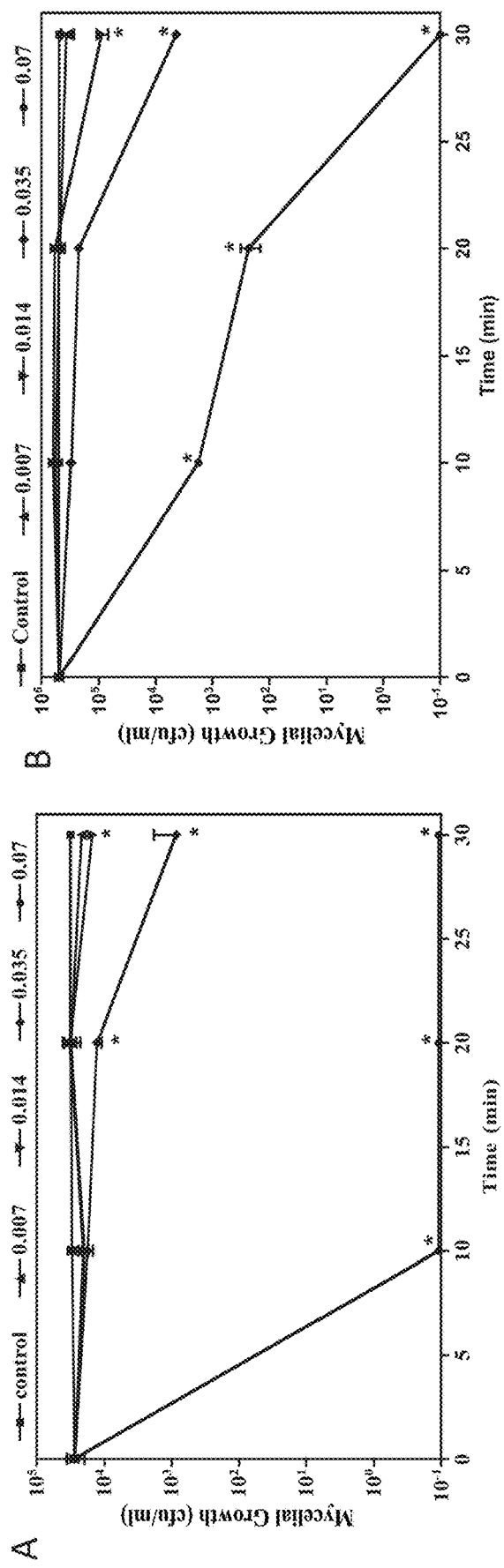
FIG. 10 is a graph depicting the antifungal efficacy of NORS against *Trichophyton mentagrophytes* (10A) and *Trichophyton rubrum* (10B) using NORS of varying nitrite concentrations (0.007-0.07%). Error bars indicate standard deviation for three experiments with 3 repetitions each. A* represents significant (P<0.05) difference from control.

FIG. 10 shows the mycelia viability following exposure as a percentage of control. *T. mentagrophytes* (FIG. 10A) and *T. rubrum* (FIG. 10B) both demonstrated similar responses to different concentrations of NORS. Both species were tolerant to up to 0.014% w/v nitrite at pH 3.7 for up to 20 minutes demonstrating a reduction of less than 25%. While using a higher concentration of 0.035% w/v nitrite at pH 3.7 rendered a time dependent fungicidal effect starting from a significant 25% reduction after 10 minutes and reaching a 98% reduction after 30 minutes for both species. An increase to 0.7% w/v nitrite and 0.08% w/v citric acid was highly effective at eradicating mycelia resulting in a greater than 99% reduction at 10 minutes and complete kill at 30 minutes for *T. mentagrophytes* and a complete kill at all time points for the *T. rubrum*. Not surprisingly a concentration of 0.14% w/v nitrite at pH 3.7 showed a complete kill, even after 10 minutes, for both organisms (not shown on graph).

Controls with citric acid at pH 3.7, and nitrites alone, had no significant effect on mycelial growth when compared to water control.

Analysis of Head Space Gases Above NORS Using GC-MS.

Figure 11A:
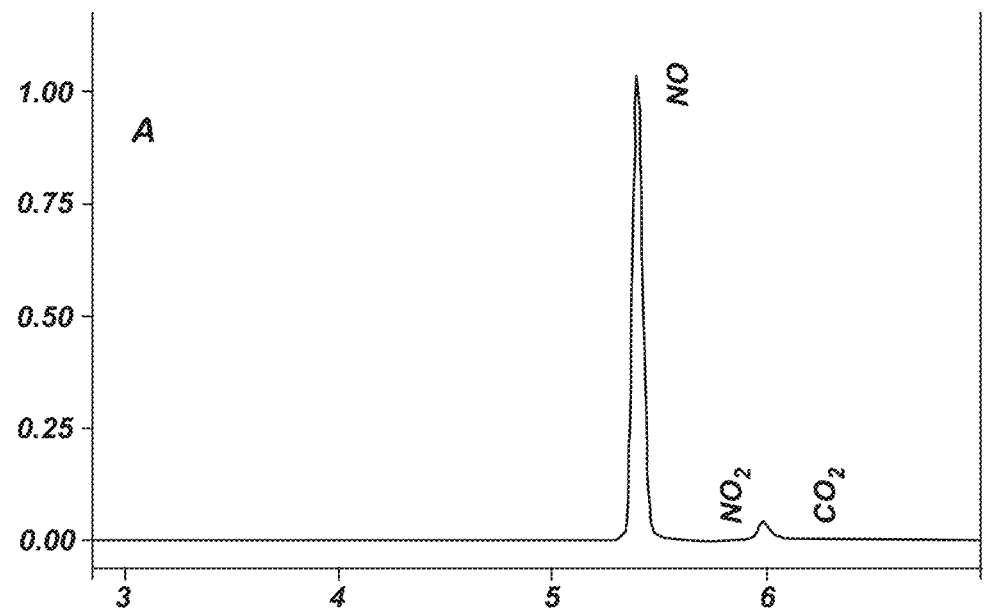
FIGS. 11A-11B is a chromatogram of head space gases found after 30 minutes of NORS exposure. Shown is a chromatogram produced by a GC-MS demonstrating the constituents of the headspace gas following 30 min exposure of 0.14% NORS. GC-MS method was calibrated to quantify NO, $N_2O$, and $NO_2$ levels. A—GC chromatogram for MW=30-molecules detected are labeled above each peak. B—MS chromatogram with the molecular weight detected at 5.4 min.
Figure 11B:
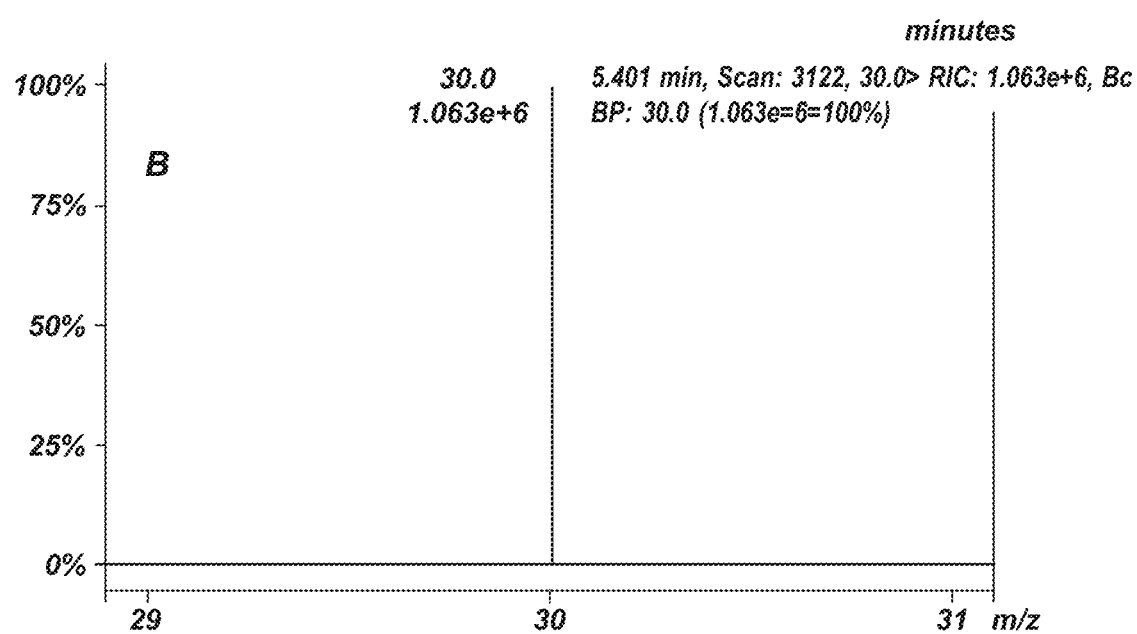

A head-space sample from the tube (containing 4 mL of 0.14% NORS) after 20 minutes was analyzed by GC-MS to determine which gaseous molecules could be detected. Specific detection was set to identify NO, $NO_2$, $N_2O$ and $CO_2$ and their respective concentrations were determined. As revealed by the chromatogram in FIG. 11A, three types of gas molecules were detected (excluding water vapor, not shown). NO eluted at 5.4 minutes, $NO_2$ at 5.98 and $CO_2$ eluted at 6.03 minutes. No other peaks were detected in a scan program for MW 18-100. FIG. 11B shows the molecular weight of 30 for the peak at 5.4 minutes, which correlates to NO. NO concentration was found to be 170(±30) ppm; $NO_2$ was 40(±10) ppm. $CO_2$ (coming from ambient air) was found as well but not quantified. $N_2O$ was not detected. As a comparison, headspace from a control tube had only ambient levels of $CO_2$ present in it.

Figure 12:
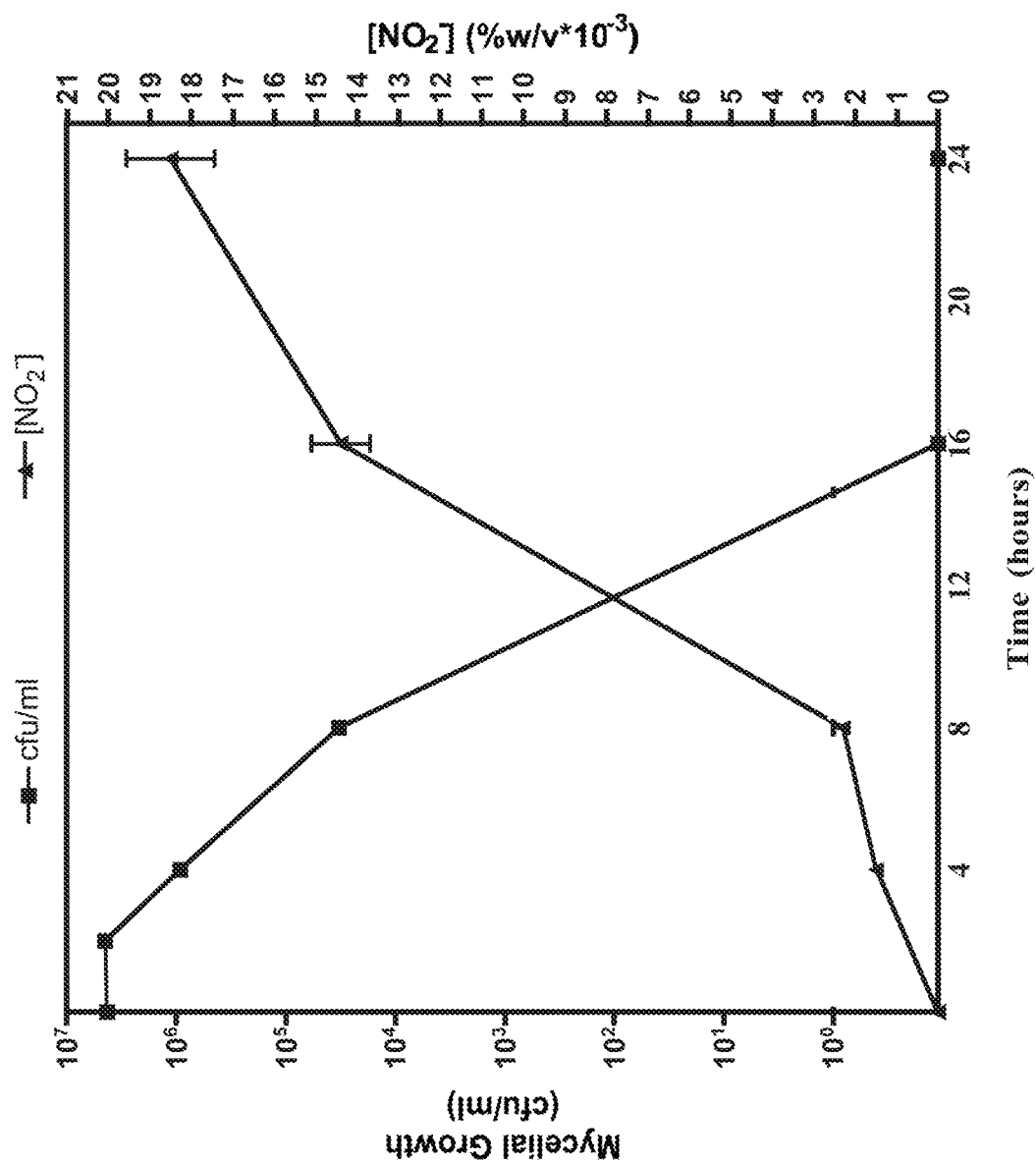
FIG. 12. Antifungal activity of the head space gases produced from NORS. Two line graphs demonstrating 1. Viability count of *T. mentagrophytes* mycelia (left Y axis) and 2. Nitrite levels in the exposed fungi solution (right Y axis) measured by Griess Reagent™ Both, after being exposed to gases generated from NORS into the headspace for 2, 4, 8, 16, and 24 hours. Mycelial viability count is shown as squares while nitrite concentration is shown as triangles. Error bars indicate standard deviation from triplicates.

In order to demonstrate that the NO being produced by the NORS is likely the active agent responsible for the antifungal activity observed, an apparatus was constructed to ensure no direct contact occurred between fungal mycelia and the NORS, allowing only for the exchange of headspace gases (FIG. 9). The antifungal activity of the NORS headspace gases was tested on *T. mentagrophytes* mycelia at 1 mg/mL. Both mycelial viability and nitrite concentrations were measured after 2, 4, 8, 16, and 24 hours. FIG. 12 illustrates the antifungal activity of the NORS gases over a 24 hour period. Some antifungal effect was observed after 4 and 8 hours of exposure, where a one $\log_{10}$ reduction in mycelial viability was observed. Complete kill resulted after 16 hours of exposure. Mycelia controls showed no significant change in concentration during these time periods. Nitrite concentrations were shown to inversely correlate with mycelial viability. Following 16 hours, where complete kill of the mycelia was reached, a nitrite concentration of 0.014% w/v was measured. Mycelia controls showed nitrite concentrations to be negligible. When using saline in the apparatus, instead of NORS, no mycelial kill was found and no NO was found in the headspace.

Example 7: Prophylactic Nitric Oxide Treatment Reduces Incidence of Bovine Respiratory Disease Complex in Beef Cattle Arriving at a Feedlot In further demonstration of the overall effectiveness of the present invention to also combat similar diseases in mammalian species, the results described herein demonstrate that NO treatment on arrival to the feedlot significantly decreased the incidence of BRDc in beef cattle. Eighty-five, crossbred, multiple-sourced, commingled commercial weaned beef calves were monitored and scored for temperature, white blood count, clinical score, hematology, cortisol levels and neutrophil/lymphocyte ratio. NO treatment or placebo was given once on arrival to the stockyard. After one week, 87.5% of sick animals were from the control while 12.5% were from treatment groups, and after two weeks 72% and 28% respectively. Treatment was shown to be safe, causing neither distress nor adverse effects on the animals.

The materials and methods employed in these experiments are now described.
Animals and Management Eighty-five, crossbred, multiple sourced, commingled commercial weaned beef calves were obtain for these studies. All studies were conducted at the Lacombe Research Centre beef research facility and all management practices followed Canadian Council of Animal Care guidelines (Canadian Council on Animal Care, 1993) and Canadian Beef Cattle Code of Practice guidelines (Agriculture Canada, 1991). In addition, the research protocols were reviewed and approved by the Lacombe Research Centre animal care committee. The calves were procured through a conventional auction system and all animals had been exposed to between 4-6 h of transport prior to the study. These calves were chosen in order to provide study groups displaying a BRDc incidence range of 30-60% which is typical of the beef industry in Canada for these "put together" herds of cattle. On arrival at Lacombe the calves were off loaded, weighed, sampled for saliva and blood using procedures described previously (Schaefer et al., 2012, Virulence 3:271-279).

The calves were randomized into treatment and control groups, labeled with color coded ear tags and numbers. Animals were then placed into outdoor pens measuring approximately 60×60 meter and were bunk feed ad libitum a balanced cereal silage diet, which met or exceeded National Research Council recommendations (NRC, 1984, Nutrient Requirements of Beef Cattle, 6th ed. National Academy Press, Washington, D.C.). The animals also had free access to water and were provided a straw bedding area with a roof covering.
Clinical Scores While contained in their receiving pens the calves were monitored daily by trained personnel, whom were blinded as to the treatment interventions, for clinical signs of illness using methods described previously (Schaefer et al., 2007, Res. Vet. Sci. 83:376-384). Briefly, clinical scores were designed to identify BRDc and were based on the appearance of four criteria as follows:

Respiratory insult: (0-5): 0=no insult, normal breath sounds (NBS); 1=Very Fine Crackle (rale) (VFCR) on auscultation and/or a moderate cough; 2=Fine Crackle (subcrepitant) (FCR) on auscultation and/or a moderate nasal discharge and moderate cough; 3=Medium Crackle (crepitant) (MCR) on auscultation and/or a moderate to severe viscous nasal discharge with cough; 4=Course Crackles (CCR), tachypnea (>15% of the norm) and/or a severe nasal discharge with respiratory distress and obtunded lung sounds and 5=CCR with dyspnea, tachypnea, marked respiratory distress and/or lung consolidation.

Digestive insult: (0-5): 0=no insult, normal, eating and drinking; 1=mild or slight diarrhea with slight dehydration (<5%) and reduced eating; 2=moderate diarrhea with 10% dehydration and reduced feed intake (<50%); 3=moderate to severe diarrhea with 10% or less of feed intake and more than 10% dehydration; 4=severe diarrhea, and less than 10% of normal feed intake and 5=severe diarrhea and not eating, not drinking and dehydrated.

Temperature score: Core temperature (rectal) (0-5): 0=<37.7° C.; 1=37.7-38.2° C.; 2=38.3-38.8° C.; 3=38.9-39.4° C.; 4=39.5-40.0° C. and 5=>40° C. Rectal or core temperatures for the calves were collected at the start and end of the study only as these were the times that the animals were restrained. Disposition or lethargy score: (0-5): 0=no lethargy, normal posture; 1=mild anorexia or listlessness, depressed appearance; 2=moderate lethargy and depression, slow to rise, anorectic; 3=recumbent or abnormal posture, largely depressed; 4=prostrate, recumbent or abnormal posture and 5=death.
Laboratory Analysis With respect to laboratory analysis, salivary and serum cortisol levels were analyzed using an enzymatic assay previously described (Cook et al., 1997, J. Ag. Food Chem. 45:395-399).
Hematology Hematology values were measured on a Cell-Dyn 700 Hematology Analyzer (*Sequoia*—Turner Corp. Mountain View, Calif.). Differential blood cell counts were determined utilizing stained blood smears (Geisma-Wright quick stain) and direct microscope examination of 100 cells.
Clinical Rescue Treatment Animals displaying overt clinical symptoms of BRDc as identified by a blinded pen keeper were rescued and subsequently received immediate treatment as recommended by the Lacombe Research Centre veterinarian followed by continued monitoring and re-treatment if required. These animals were classified as true positive (TP) in the statistical analysis.
Nitric Oxide Treatment NORS was delivered with a spray device. The NORS is a saline based solution having a citric acid concentration of about 0.2% w/v and sodium nitrite concentration of 0.41% w/v. This solution was previously tested and verified to release 160 ppm NO in a 3 L/m flow of medical air (Praxair, Canada), for 30 min. In brief, 32 mL of the solution was sprayed into a two inch diameter vinyl chloride tube and inserted into environmentally controlled system (as previously described by Ghaffari et al., 2005) where NO was measured using chemiluminescence (Sievers Nitric Oxide Analyzer NOA 280i). Animals were restrained in a conventional hydraulic cattle-handling catch and given either a placebo (saline) or treatment (NO) by an individual blinded as to the intervention. Each animal received 1 spray (8 mL), alternating into each nostril, twice, for a total of 32 mL before being released into the feeding lot pen areas. The duration of treatment administration was less than 5 s.

Determination of True Positive (TP) and True Negative (TN) Animals for Bovine Respiratory Disease Complex (BRDc)

The determination of an animal true positive or negative for BRDc was based on the comparison to a set of "gold standard" values using a previously published method (Humblet et al., 2004, Res. Vet. Sci. 77:41-47; Schaefer et al., 2007, Res. Vet. Sci. 83:376-384). This approach is commonly promoted in both veterinary and human medical diagnostic studies (Galen and Gambino, 1975, Beyond Normality. J. Wiley and Sons, NY; Thrusfield, 1995, Diagnostic testing, p. 266-285, Veterinary Epidemiology, $2^{nd}$ ed. Blackwell Sci. Ltd., Oxford).

In the current study, the criteria for a true positive animal for BRDc was defined as an animal displaying three or more of the following signs; a core temperature of >40° C. (or 103.5° F.), a white blood cell count of less than 7 or greater than 11×1000/L, a clinical score of >3 or a neutrophil/lymphocyte ratio of <0.1 (leucopenia) or >0.8 (neutrophilia). A true negative animal was defined as an animal displaying a score of 0 or 1. These parameters were considered consistent with suggested normal and abnormal ranges (Kaneko, 1980, Clinical Biochemistry of Domestic Animals, Academic Press, NY; Blood et al., 1983, Veterinary Medicine, $6^{th}$ ed., Communications Branch, Agriculture Canada). For laboratory assessments, all calves were monitored at the beginning of the study and again three to four weeks later.

The results of the experiments are now described.

Safety of NO Treatment

All animals tolerated the nitric oxide treatments well. Some of the animals sneezed but none exhibited coughing or other clinical signs of distress. There were no adverse events nor serious adverse events observed in either cohort. No animals died during the time of the study. Mean salivary and cortisol levels were equivalent in each group (Control 5.4±5.7 nmol/L; Treatment 6.66±5.5 nmol/L) without a significant differences (p=0.09).

Decreased Incidence of BRDc

As can be seen in Table 1, during days 1-14, 13 animals from the control group and 5 animals from the treatment group were identified as TP. The table shows values recorded for all 4 parameters determining TP/TN for all TP animals. Temperature, clinical score, white blood count, neutrophil/lymphocyte ratio were also included. All sick animals had 3 or 4 parameters recorded below or above the defining value for TP. This scoring approach provides a more robust definition of sick animals as compared to looking at just a temperature threshold alone. All animals had clinical scores above 3 and 15 out the 18 animals had temperature recorded as 103.5° F. or higher. Thirteen out of the 18 TP animals were also recognized by the pen keeper as sick.

TABLE 1

Parameters determining TP/TN

|  | Animal # | Day of sickness | Temp (° F.) | Clinical Score | WBC | N/L ratio | Pulled out |
|---|---|---|---|---|---|---|---|
| Control | 1 | 14 | 104.2 | 8 | 9.58 | 0.027 | Y |
|  | 2 | 14 | 103.8 | 4 | 11.1 | 0.121 | Y |
|  | 3 | 14 | 103.6 | 5 | 5.97 | 0.139 | Y |
|  | 4 | 7 | 105.2 | 8 | 6.38 | 0.721 | Y |
|  | 5 | 2 | 104.1 | 8 | 7.97 | 0.092 | Y |
|  | 6 | 4 | 105.8 | 7 | 2.75 | 0.882 | Y |
|  | 7 | 10 | 104.5 | 8 | 11.15 | 1.136 | Y |
|  | 8 | 9 | 103.5 | 7 | 6.61 | 0.099 | Y |
|  | 9 | 7 | 103.1 | 4 | 6.53 | 0.023 | N |
|  | 10 | 7 | 103.1 | 4 | 10.95 | 0.037 | N |
|  | 11 | 7 | 103.5 | 5 | 7.56 | 0.077 | N |
|  | 12 | 7 | 103.4 | 5 | 5.99 | 0.092 | N |
|  | 13 | 8 | 105.6 | 9 | 4.67 | 0.678 | Y |
| Treatment | 1 | 14 | 103.5 | 5 | 6.7 | 0.556 | N |
|  | 2 | 6 | 106.2 | 8 | 12.15 | 1.058 | Y |
|  | 3 | 8 | 104.2 | 10 | 6.57 | 1.537 | Y |
|  | 4 | 11 | 105.4 | 9 | 11.25 | 0.877 | Y |
|  | 5 | 8 | 104.6 | 8 | 6.72 | 0.191 | Y |

Values recorded for all 4 parameters determining TP/TN for all sick animals in both groups during the first 2 weeks after arrival to feedlot (TP indicators are highlighted).

Table includes day of recorded sickness and whether the animal was pulled out by herdsman.

In terms of a BRDc incidence in this model, of these 82 calves evaluated, after 7 days post arrival, 8 displayed true positive for BRDc (10%). As shown in FIG. 13A, 7 animal (17.5%) out of the 40 in the control group and 1 (2.4%) out of 42 in the NO treated group were identified as TP in the first week. Of these 8 animals, one (12.5%) was from the NO treated group and seven (87.5%) were from the saline control group (FIG. 13B). These results demonstrate a very significant reduction of the incidence of BRDc between the treatment and control cohorts with a single NORS treatment upon arrival into the stockyard (p<0.001). During the first 14 days, 18 animals (22%) had an incidence of BRDc and of these 13 (72.2%) were in the control group whereas only 5 (27.8%) were in the treatment cohort (FIG. 13B).

These data, collected from three separate randomized and blinded studies performed in a conventional feedlot, show that NO significantly decreased the incidence of BRDc, as defined by true positive rigor, by a difference of 75% as compared to a saline placebo (87.5% of sick animals were from control group versus 12.5% from treatment group.

Example 8: Bioavailability of Nitric Oxide to Control Bovine Respiratory Disease Complex in Calves Entering a Feedlot The results described here demonstrate that the delivery of NORS to a bovine's nostril is biologically available. Thirteen, crossbred, multiple-sourced, commingled commercial weaned beef calves were treated multiple times intranasally over a 4 week period with either a nitric oxide releasing solution (treatment) or saline (control). Exhaled NO, methemoglobin percent (MetHb) and serum nitrites demonstrated biological availability as a result of treatment.

The materials and methods employed in these experiments are now described.

Animals and Management

The study was conducted at a commercially registered feedlot facility in Western Canada (Westwold, British Columbia). All management practices followed the Canadian Council of Animal Care guidelines (Canadian Council on Animal Care, 1993) and Canadian Beef Cattle Code of Practice guidelines (Agriculture Canada, 1991). In addition, the research protocols adhered to the Experimental Study Certificate approved by the Health Canada Veterinary Drug Directorate and the Thompson Rivers University animal care committee.

Thirteen, crossbred, multiple-sourced, commingled commercial weaned beef calves were procured through a conventional auction system. All animals were exposed to approximately 4-6 hours of transport prior to the study. These calves were chosen in order to provide study groups displaying a BRDc incidence range of 30-60% which is typical of the beef industry in Canada for this type of a cattle population. On arrival at the feedlot the calves were off loaded, randomized into one of three cohorts, received ear tags, were vaccinated (Bovi-Shield® GOLD FP™ 5; Pfizer, INFORCE™ 3; Pfizer, Mannheimia Haemolitica Bacterin-Toxoid; Pfizer) and weighed.

Calves consisted of 3 groups as follows: 1) Control group—received saline as placebo (n=4), 2) Treatment group—2 sprays of NO treatment in each nostril—32 mL in total (n=5) and 3) Treatment group with 5 times the normal NO treatment dose of 160 mL in total in each treatment. All groups were treated with NO on arrival approximately 2 minutes after giving the vaccines. Animals were then placed into 2 outdoor corrals, separated into control or treatment groups. They were fed chopped hay, grain screening pellets, along with alfalfa/grass and barley silage to provide a complete ration which met or exceeded National Research Council recommendations (NRC, 1984). The animals also had free access to water and were provided with sawdust bedding.

Nitric Oxide Treatment

A nitric oxide releasing solution (NORS) was prepared in a 5 L spray device, which contained 2 L of the NORS. The NORS is a saline based solution having a citric acid concentration of about 0.2% and sodium nitrite concentration of about 0.41% (60 mM). The solution was prepared on site just prior to administration. This solution was previously tested to release 160 ppm NO in a 3 L/min flow of gas as verified by chemiluminescence analysis (280i, General Electric, CO). Animals were briefly restrained in a conventional hydraulic cattle handling squeeze and given either saline or NORS by a trained research assistant. Each animal in the control and normal treatment dosing groups received 1 spray (8 mL), alternating into each nostril, for a total of 32 mL of either of the interventions before being released into the feeding lot pen areas. Each animal in the second dosing group received 5 times the above-described dosing volume, for a total of 160 mL. Animals received these treatments weekly for four consecutive weeks.

Laboratory Analysis

Blood samples were collected on day 14. Blood was collected by a licensed veterinarian via jugular venipuncture before treatment, 5 minutes post treatment and 30 minutes post treatment interventions. Each sample was placed in one of 3 appropriately prepared collection tubes—one for each measurement: Cortisol, methemoglobin percent (MetHb) and nitrites. Serum cortisol was analyzed by Kamloops Large Animal Veterinary Clinic LTD. (1465 Cariboo Place, Kamloops, BC V2C 5Z3). All blood samples were transferred to Thompson River University (TRU) on ice for measurements of MetHb. Blood gas analysis was done for co-oximetric measurement of MetHb using an ABL 800 FLEX analyzer (Radiometer America Inc., Ohio, USA). Blood gases including arterial oxygen, carbon dioxide, pH, bicarbonate and electrolytes were also measured at that time.

Measurement of Exhaled NO

Fractional exhaled concentration of NO ($F_E NO$) was measured using a chemiluminescence analyzer (280i, GE, CO). A $F_E NO$ baseline measurement was obtained for each subject by recording for 1 minute before and after treatment intervention until $F_E NO$ levels returned back to baseline. The sampling tube had a water filter to prevent liquid from getting into the device. The filter was at the distal end and was held as close as possible to the animal's nostril. All of the animal handling was performed by the same person to reduce handler variation. The machine was calibrated before each use with standard calibration gases as per manufacturer's instructions.

Nitrite Measurements

Blood samples for nitrite analysis were collected on day 14 (as described above). All samples for nitrite measurement were placed in heparinized tubes and centrifuged for 5 minutes at 5000 RPM. The supernatant was recovered and placed in Eppendorff tubes, placed on dry ice, and then samples were immediately transferred to a −80° C. freezer until processing. Nitrite measurements were performed using a chemiluminescent liquid interface technique according to the manufacturer's instructions (280i, General Electric, CO).

The results of the experiments are now described.

Bioavailability Measurements

All three parameters measured for bioavailability (MetHb, $F_E NO$ and nitrites in serum) showed biochemical changes within 5 minutes post treatment.

MetHb Measurements

Figure 14B:
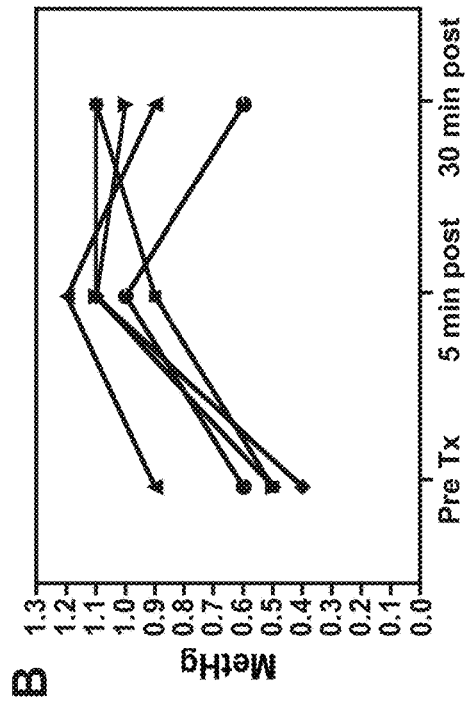
FIGS. 14A-14C depicts MetHb levels.
Figure 14A:
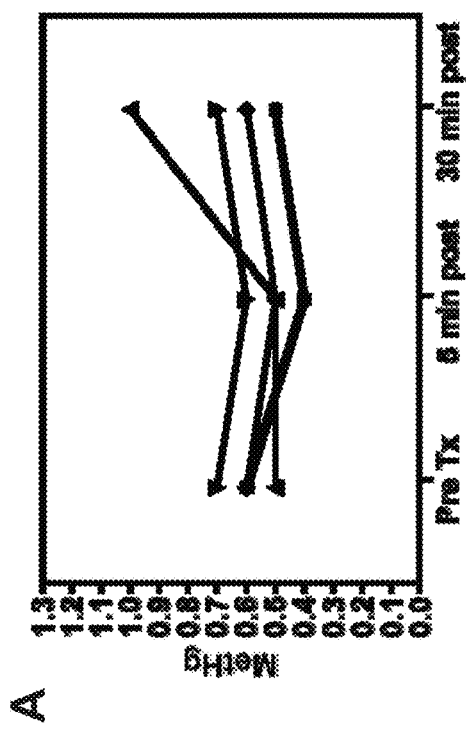
Figure 14C:
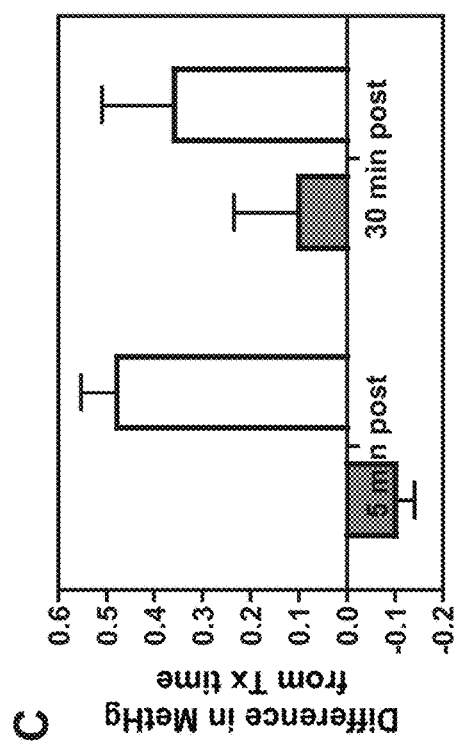

MetHb was measured using Cooximetry on blood samples taken before treatment and at 5 and 30 minutes post treatment with either NORS or saline control. The saline control group (FIG. 14A) did not have any significant difference between MetHb values before and after treatment. On the other hand, the NORS treatment group had higher values of MetHb 5 and 30 minutes after administering the treatment (FIG. 14B). FIG. 14 depicts the values of MetHb for the control and treatment group animals (FIGS. 14A and 14B, respectively), and the average difference between the MetHb value at 5 and 30 minutes post treatment, compared to baseline (FIG. 14C). There was a significant difference observed at the 5 minute post-treatment time between the NORS and the saline control group. The MetHb value was, on average, 4.8 points higher in the treatment group compared to 0.1 lower in the control group. Small but insignificant differences were found after 30 min between treatments, although for the NORS treatment group, values stayed significantly higher than the baseline measure.

Measurement of $F_E NO$

Figure 15B:
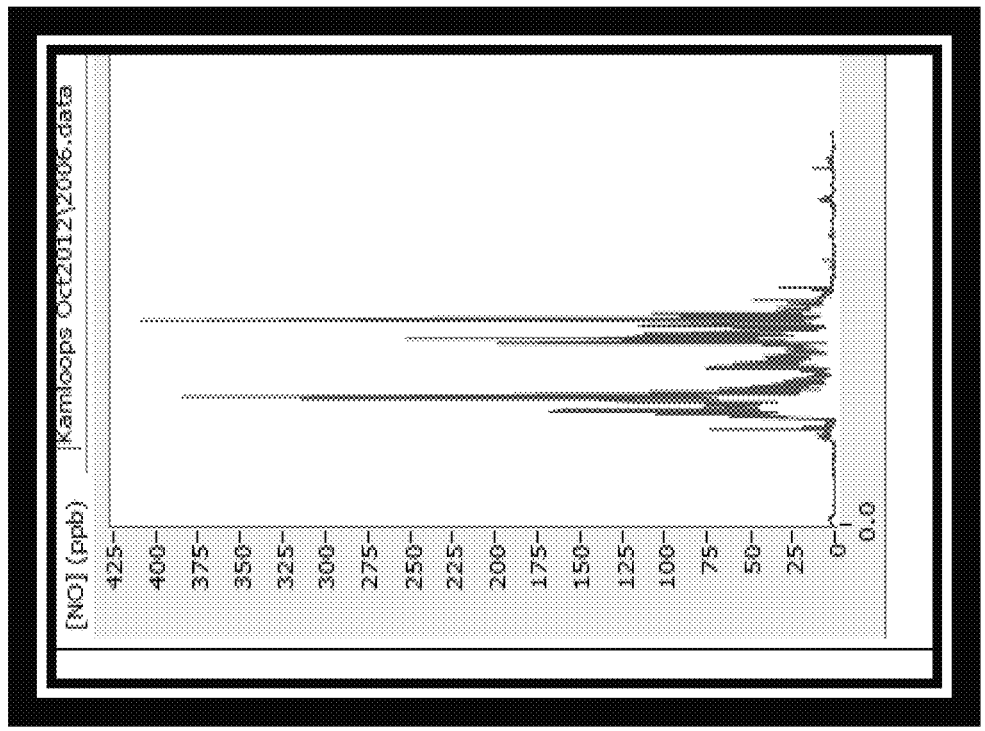
FIGS. 15A-15B depicts the exhaled NO measured by chemiluminescence.
Figure 15A:
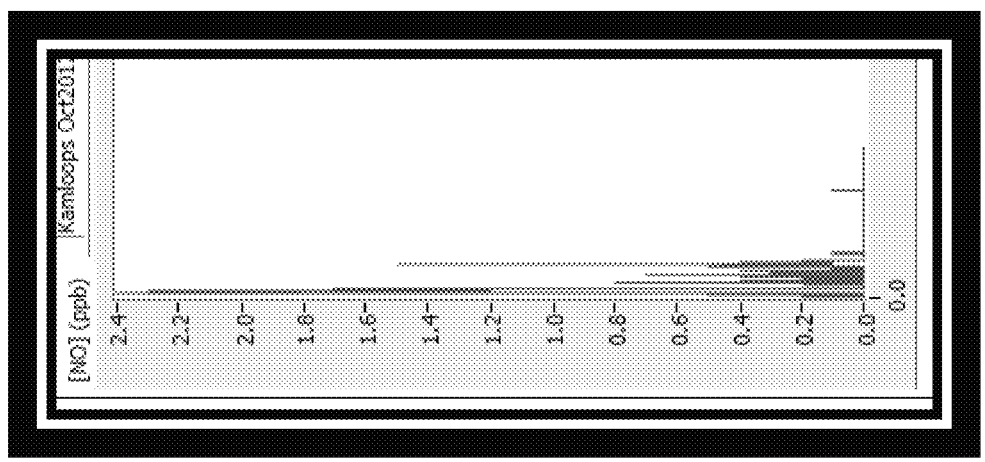

When administering NORS to the animal, the $F_E NO$ were high enough to be detected by chemiluminescent analysis within seconds to minutes following the NORS treatment (FIG. 15). FIG. 15A depicts the $F_E NO$ measured after giving saline to the animal (2.4 ppb) while FIG. 15B shows $F_E NO$ after giving NORS (around 400 ppb for approximately 5 minutes). This was measured outside the nostril, while diluted with air, and thus levels are much lower than actual $F_E NO$ levels. However, this result demonstrates that the NO gas is present compared to the saline control.

Nitrites in Serum

Figure 16:
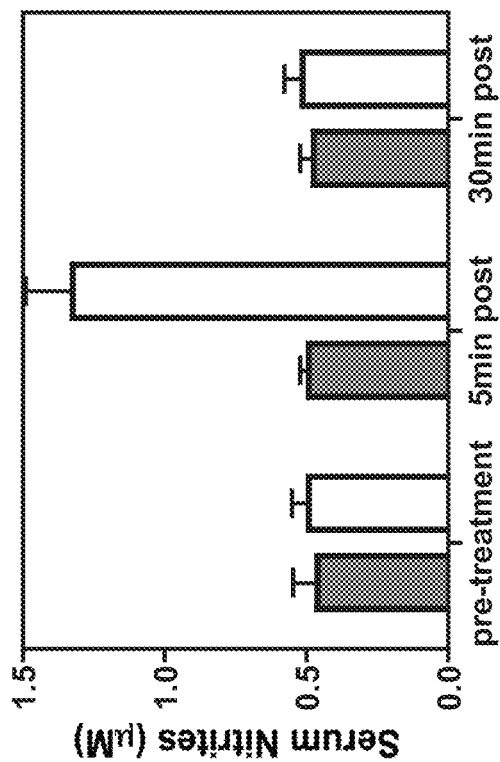
FIG. 16 depicts nitrite concentration in samples. Figure is a showing the difference in nitrite concentration in samples after treatment (concentration in the 5 minute or 30 minutes post-treatment samples minus the concentration in the pre-treatment samples). (grey=control, white=NO treatment) Error bars indicate standard deviation for all animals tested in each group.

Nitrites were measured using the chemiluminescence liquid interface technique. Samples were extracted with cold ethanol and 50 µl was injected. As seen in FIG. 16, 5 minute post treatment there was a raise in the nitrite concentration in the animal's serum. By 30 minutes post treatment there was no significant difference (P>0.05) from the control group.

These results described herein demonstrate that NORS at 0.41% resulted in NO bioavailability, which was confirmed by the rise of $F_E NO$ in the treated animal and by the expected transient rise in MetHb percent, indicating that NO was available within the respiratory tract and metabolized in the serum into increased nitrite levels.

Example 9: Ferrets Study with NORS

This experiment was performed to test the effect of NORS on temperature and blood nitrites in ferrets, after Influenza A infection.

The materials and methods employed in these experiments are now described.

Six 10-12 week-old ferrets were purchased from Triple F Farms and acclimated for 5-7 days prior to challenge. They were housed loose and together in a 12×18 ft. room for the duration of the study.

Figure 17:
FIG. 17 comprised of two photos depict the administration of NORS as a mist to ferrets.
Figure 17:

Six ferrets were stable for the study were anesthetized with ketamine-xylazine and bled for nitrite baseline values. All animals were challenged with Influenza A/California/04/2009 virus by intranasal instillation of approximately $7.5 \times 10^4$ pfu in 0.5 mL. Animals were then bled again to assess serum nitrite levels. Blood samples were obtained 30 and 240 minutes post treatments and analyzed for serum nitrites with a chemiluminescent analyzer. Within 5-10 minutes of inoculation treatment interventions were administered. One cohort of ferrets (n=3) received approximately 2 mL NORS over a ten minute period with a small volume nebulizer at 7 L/min. Another cohort of ferrets (n=3) received approximately 2 mL saline over a ten minute period with a small volume nebulizer at 7 L/min (FIG. 17)

The results were analyzed using the unpaired Student's t-test for comparison between any two groups. Group means were statistically tested by least squares means (two-tailed t-test). For experiments with multiple (more than 2) sets, Statistical analysis of data obtained were performed using a one-way analysis of variance (ANOVA) and Tukey's Multiple Comparison Test Data analysis and graphical presentation were done using a commercial statistics package (Graphpad-Prism V 3.0, GraphPad Software Inc., USA). Unless otherwise specified, p<0.05 indicated statistical significance. Results were reported as the mean±standard deviation.

The results of the experiments are now described.

Figure 18A:
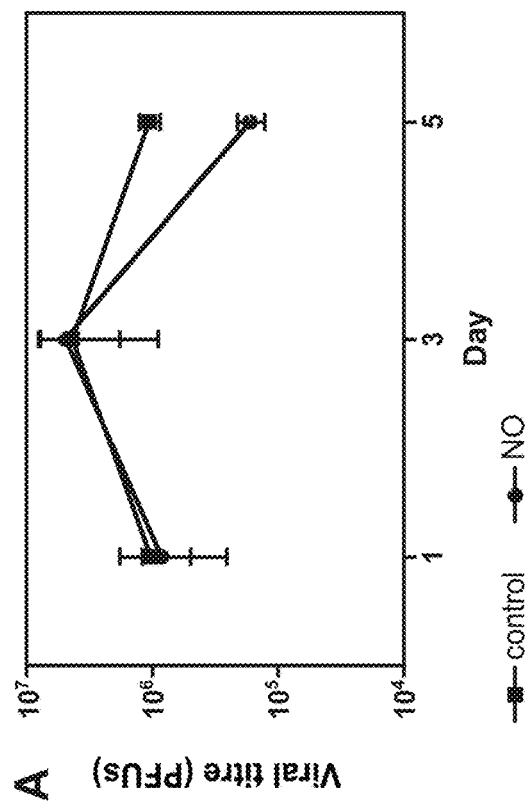
FIGS. 18A-18B depict the changes in temperature (18A) and viral titre (18B) 1-5 days post viral installation and treatment with either saline (control) or NORS (0.41%) to ferrets.

Nitrites in the serum were significantly elevated at 30 minutes (p<0.05) and returned to baseline after 240 minutes post NORS treatment as compared to baseline values (FIG. 18A). Moreover, when the NORS treatment\was administered, there were significant levels of NO detectable by AeroNOx™ (Pulmonox, Canada) device. These results show that the bioavailability of NO produced from NORS was demonstrated in the serum after treatment.

Figure 18B:
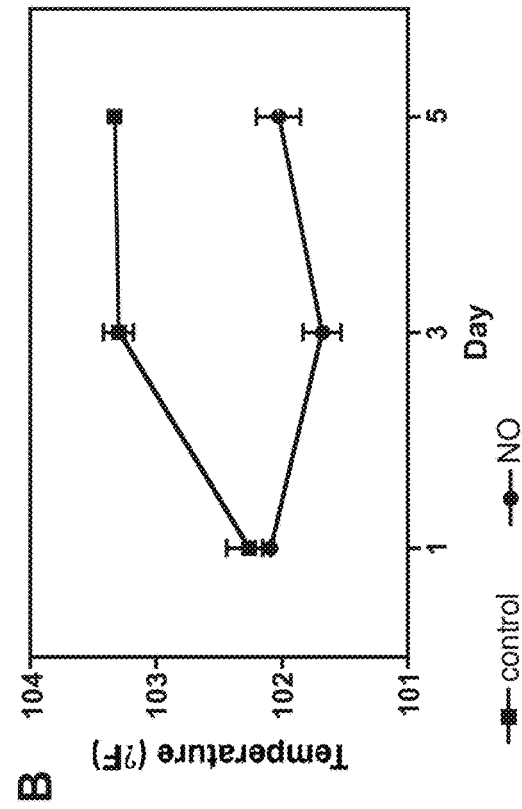

The average temperature for control versus treated animals, after 3 and 5 days was significantly (P<0.05) higher (FIG. 18B). This shows a systemic effect of the NORS treatment on the ferrets.

The invention claimed is:

1. A liquid nitric oxide releasing solution (NORS) comprising at least one nitric oxide releasing compound and at least one acidifying agent, wherein the NORS provides an extended release of a therapeutically effective amount of nitric oxide gas (gNO), wherein the gNO is released over a period of at least 30 minutes, and wherein either the amount of the at least one nitric oxide releasing compound is not greater than about 0.5% w/v, or the amount of the at least one acidifying agent is not greater than about 0.5% w/v, and wherein the NORS has a pH of from about 1 to about 4 during gNO release.

2. The solution of claim 1, wherein the at least one nitric oxide releasing compound is selected from the group consisting of a nitrite, a salt thereof, and any combinations thereof.

3. The solution of claim 2, wherein the nitrite is sodium nitrite.

4. The solution of claim 1, wherein the amount of the at least one nitric oxide releasing compound is not greater than about 0.5% w/v.

5. The solution of claim 1, wherein the at least one acidifying agent is an acid.

6. The solution of claim 5, wherein the acid is citric acid.

7. The solution of claim 1, wherein the amount of the at least one acidifying agent is no greater than about 0.5% w/v.

8. The solution of claim 1, wherein the therapeutically effective concentration of NO is about 160 ppm.

9. The solution of claim 1, wherein the NORS is a saline-based solution.

10. The solution of claim 1, wherein the gNO is released over a period of at least 4 hours.

11. The solution of claim 1, wherein the gNO is released over a period of at least 8 hours.

12. The solution of claim 1, wherein the gNO is released over a period of at least 12 hours.

13. The solution of claim 1, wherein the gNO is released over a period of at least 24 hours.

* * * * *